United States Patent [19]

Cragoe, Jr. et al.

[11] 4,012,524

[45] Mar. 15, 1977

[54] [1-HYDROXY-5-INDANYLOXY (OR THIO)]-ALKANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: June 10, 1975

[21] Appl. No.: 585,435

Related U.S. Application Data

[63] Continuation-in-part of Ser. No. 492,944, July 31, 1974, abandoned, which is a continuation-in-part of Ser. No. 405,965, Oct. 12, 1973, abandoned.

[52] U.S. Cl. .......................... 424/308; 260/308 D; 260/332.2 A; 260/473 F; 260/520 C; 424/269; 424/275; 424/317

[51] Int. Cl.² .............. A61K 31/235; A61K 31/19; A61K 31/41; C07D 257/04

[58] Field of Search ......................... 424/317, 308; 260/520 C, 473 F

[56] References Cited

UNITED STATES PATENTS 3,668,241   6/1972   Cragoe, Jr. et al. ............ 424/317 X

OTHER PUBLICATIONS

Koelsch et al., J. Am. Chem. Soc., 65, 2311 (1943).

*Primary Examiner*—Frederick E. Waddell
*Attorney, Agent, or Firm*—Michael C. Sudol, Jr.; J. Jerome Behan

[57] ABSTRACT

[1-Hydroxy-5-indanyloxy (or thio)]alkanoic acids and their salts, esters and amides are disclosed. The products display a dual pharmaceutical utility in that they exhibit diuretic, saluretic and hypouricemic activity. The acid products are prepared by several synthetic methods.

13 Claims, No Drawings

[1-HYDROXY-5-INDANYLOXY (OR THIO)]-ALKANOIC ACIDS

CROSS REFERENCES TO OTHER APPLICATIONS

This application is a continuation-in-part of our co-pending application Ser. No. 492,944 filed July 31, 1974, now abandoned which in turn is a continuation-in-part of our co-pending application Ser. No. 405,965 filed Oct. 12, 1973 now abandoned.

BACKGROUND OF THE INVENTION

This application describes processes and novel products, some of the starting or intermediate materials for which are described in two United States issued patents assigned to the same assignee, Nos. 3,704,314 and 3,668,241.

This invention relates to a new class of chemical compounds which can be described generally as [1-hydroxy-5- indanyloxy(or thio)]alkanoic acids and to the non-toxic, pharmacologically acceptable salt, ester and amide derivatives. It is also an object of this invention to describe methods for the preparation of the [1-hydroxy-5-indanyloxy]- alkanoic acids. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may cause precipitation of uric acid or sodium urate, or both, in the body which may cause from mild to severe cases of gout. The instant compounds of this invention now provide an effective tool to treat those patients requiring diuretic and saluretic treatment without incurring the risk of inducing gout.

The [1-hydroxy-5-indanyloxy(or thio)alkanoic acids (I) of the invention have the following structural formula:

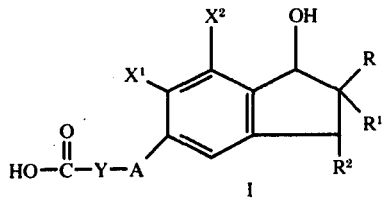

wherein A is oxygen or sulfur; R is lower alkyl containing from 1 to 5 carbon atoms such as methyl, ethyl, n-propyl, isopropyl, n-butyl, isobutyl, tert-butyl, n-pentyl and the like; cycloalkyl, for example, cycloalkyl containing from 3–6 nuclear carbon atoms such as cyclopropyl, cyclobutyl, cyclopentyl, cyclohexyl and the like, phenyl or substituted phenyl wherein the substituents are lower alkyl or halo; thienyl or substituted thienyl wherein the substituents are lower alkyl or halo; $R^1$ is hydrogen, lower alkyl containing from 1 to 5 carbon atoms such as methyl, ethyl, n-propyl, isopropyl, n-butyl, isobutyl, tert-butyl, n-pentyl and the like, phenyl lower alkyl wherein the lower alkyl contains from 1 to 3 carbon atoms such as benzyl, phenethyl, phenylpropyl and the like, phenyl or substituted phenyl wherein the substituents are lower alkyl or halo; thienyl or substituted thienyl wherein the substituents are lower alkyl or halo; or suitable groups within the above definitions of R and $R^1$ may be joined together with the carbon atoms to which they are attached to form a cycloalkyl radical containing from 3 to 7 nuclear carbon atoms which may be unsubstituted or lower alkyl substituted, for example, cyclopropyl, cyclobutyl, cyclopentyl, cyclohexyl, cycloheptyl, methylcyclopropyl and the like; $R^2$ is hydrogen, aryl, such as phenyl or lower alkyl containing from 1 to 5 carbon atoms or $R^1$ and $R^2$, taken together with the carbon atoms to which they are attached, is cycloalkyl, $X^1$ is hydrogen, methyl or halo such as chloro, bromo, fluoro and the like and $X^2$ is methyl or halo such as chloro, bromo, fluoro and the like or $X^1$ and $X^2$ may be joined to form a hydrocarbylene chain containing from 3 to 4 carbon atoms, for example, trimethylene, tetramethylene, 1,3-butadienylene and the like, and Y is an alkylene or haloalkylene radical having a maximum of 4 carbon atoms which contain from 1–3 linear carbon atoms between the oxy (or thio) and carboxy group, for example, methylene, ethylidene, propylidene, isopropylidene, ethylene, trimethylene, fluoromethylene and the like.

The preferred embodiments of this invention are the (1-hydroxy-6,7-disubstituted-5-indanyloxylacetic acids having the following structural formula:

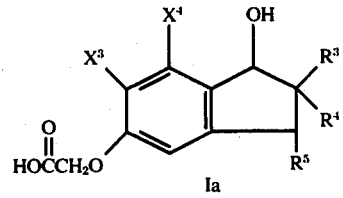

wherein $R^5$ is hydrogen or phenyl; $R^3$ is lower alkyl containing from 1 to 3 carbon atoms such as methyl, ethyl, n-propyl or isopropyl, cycloalkyl containing 5 or 6 nuclear carbon atoms such as cyclopentyl or cyclohexyl, phenyl or substituted phenyl wherein the substituents are lower alkyl or halo; thienyl or substituted thienyl wherein the substituents are lower alkyl or halo; and $R^4$ is hydrogen, lower alkyl containing from 1 to 3 carbon atoms such as methyl, ethyl, n-propyl or isopropyl; $R^5$ and $R^4$ are joined to form cycloalkyl, such as, cyclohexyl or $R^3$ and $R^4$ may be joined together with the carbon atom to which they are attached to form a cycloalkyl radical containing from 5 to 6 nuclear carbon atoms such as cyclopentyl, cyclohexyl and the like, and $X^3$ and $X^4$ are the same or different radicals selected from methyl or chloro and the non-toxic, pharmacologically acceptable salt, ester and amide derivatives. Other groups of preferred compounds within the broad generic disclosure are those compounds (with reference to formula I) in which $X^1$ and $X^2$ are the same or different and are methyl or chloro; Y is methylene; A is oxygen; $R^2$ is hydrogen and
   a. R is cycloalkyl and $R^1$ is lower alkyl;

b. R is lower alkyl and $R^1$ is hydrogen;
c. R is phenyl and $R^1$ is lower alkyl;
d. R is substituted phenyl and $R^1$ is lower alkyl;
e. R is thienyl and $R^1$ is lower alkyl;
or f. R is substituted thienyl and $R^1$ is lower alkyl.

Particularly preferred compounds within the seven groups enumerated above are those:
 a. wherein R is cyclopentyl and $R^1$ is methyl;
 b. wherein R is methyl and $R^1$ is isopropyl;
 c. wherein R is phenyl and $R^1$ is methyl or ethyl;
 d. wherein R is chlorophenyl and $R^1$ is methyl;
 or e. wherein R is thienyl and $R^1$ is methyl.

The foregoing class of compounds exhibit particularly good diuretic and saluretic activity and also either maintains the uric acid concentration in the body at pretreatment levels or even causes a decrease in the uric acid concentration.

The [1-hydroxy-5-indanyloxy(or thio)]alkanoic acids and ester (I) wherein Y contains 1 to 3 linear carbon atoms (Y') may be prepared by either of two methods. One method comprises reacting a haloacetic acid or ester thereof of the formula:

wherein $R^6$ is hydrogen or lower alkyl such as methyl, ethyl, and the like and Z is halo such as bromo, chloro, iodo and the like with a suitable 5-hydroxy(or mercapto)-1-indanol (II, infra). The following equation illustrates this reaction:

geous solvents. The reaction may be conducted at a temperature in the range of from about 25° C. to the reflux temperature of the particular solvent employed. The reaction with the haloacetic acid or ester is generally complete in about 10 to 60 minutes. If the haloacetic acid ester is employed, the ester obtained may be hydrolyzed to the free acid by methods well known to those skilled in the art.

A second method for preparing compounds of formula I wherein R is straight chain alkyl, $R^1$ is hydrogen, Y is an alkylene or haloalkylene radical having a maximum of 4 carbon atoms which contain from 1–3 linear carbon atoms between the oxy (or thio) and carboxy group, for example, methylene, ethylidene, propylidene, isopropylidene, ethylene, trimethylene, fluoromethylene and the like and $X^1$, $X^2$, $R^2$ and A are as defined above, consists of treating a 1-oxo compound (III supra) with a reducing agent such as sodium or potassium borohydride. The reaction is conducted using water or a mixture of methanol and water as a solvent and employing temperatures of 5° C. to 50° C; the reaction is illustrated as follows:

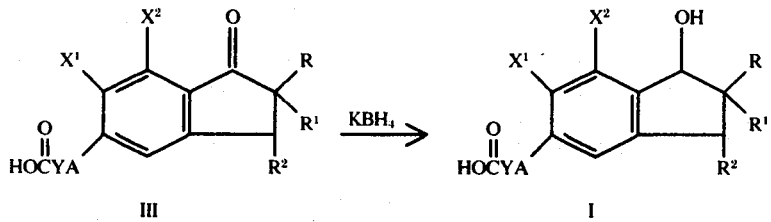

Those [1-hydroxy-5-indanyloxy-(or thio)]alkanoic acids (Id) wherein the alkylene chain contains 2 linear carbon atoms between the carboxy and oxy (or thio) groups are prepared from their corresponding 5-hydroxy (or mercaptol)-1-indanols (II) by the reaction of the latter with propiolactone or with an appropriately substituted propiolactone, in the presence of a base such as an aqueous solution of sodium hydroxide, preferably, while heating the solution at reflux temperatures; followed by the acidification of the carboxylate

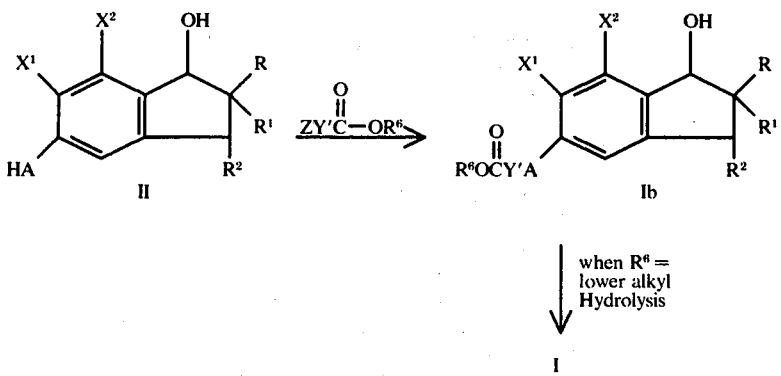

wherein $X^1$, $X^2$, R, $R^1$, $R^2$, $R^6$, Y and Z are as defined above. In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantaintermediate thus formed to the desired acid. The following equation illustrates the reaction:

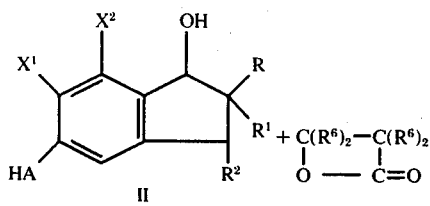

↓ MOH

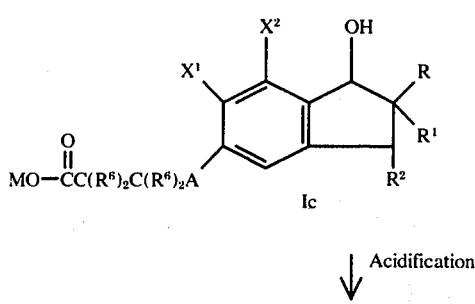

↓ Acidification wherein A, R, R¹, R², R⁶, X¹ and X² are as defined above and M is a cation derived from an alkali metal hydroxide or alkali metal carbonate such as a sodium or potassium cation.

The 5-hydroxy-(or mercapto)-1-indanols (II, supra), which also exhibit diuretic and uricosuric activity, are prepared by treating the correspondingly substituted 5-hydroxy-(or mercapto)-1-indanone (IV) with a reducing agent such as lithium aluminum hydride, sodium bis(2-methoxy-ethoxy)aluminum hydride and the like in a dry solvent such as ether, tetrahydrofuran, 1,2-dimethoxyethane and the like. The reaction is advantageously conducted at temperatures of 0° C. to 50° C. for from 5 hours to 3 days. The product is generated upon acidification of the reaction mixture with a mineral acid such as hydrochloric acid.

The following equation illustrates this process:

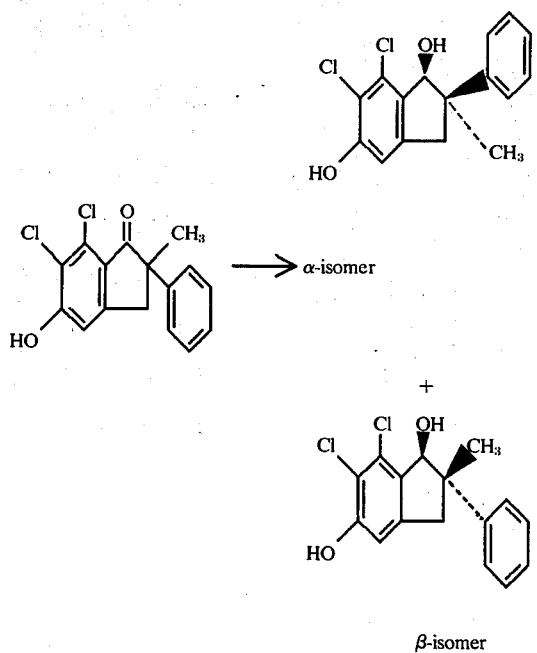

wherein A, R, R¹, R², X¹ and X² are as defined above.

In the case where R² is hydrogen and R is not the same as R¹ a mixture of α- and β-isomers is obtained. The following equation illustrates this process for the reduction of 2-methyl-2-phenyl-5-hydroxy-6,7-dichloro-1-indanone to a mixture of α- and β-isomers of 2-methyl-2-phenyl-6,7-dichloroindane-1,5-diol:

The resulting isomers are separated by crystallization from suitable solvents.

The 5-hydroxy-(or mercapto)-1-indanones (IV, supra), are prepared by treating the correspondingly substituted 5-lower alkoxy(or lower alkylthio)-1-indanone (V) with an ether cleaving reagent such as aluminum chloride, pyridine hydrochloride, sodium in liquid

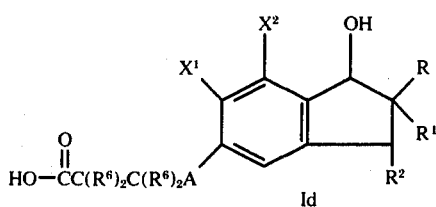

ammonia and the like. When aluminum chloride is employed, the solvent may be heptane, carbon disulfide, methylene chloride and the like and when pyridine hydrochloride is employed, it is not necessary to employ a solvent. The following equation illustrates this process:

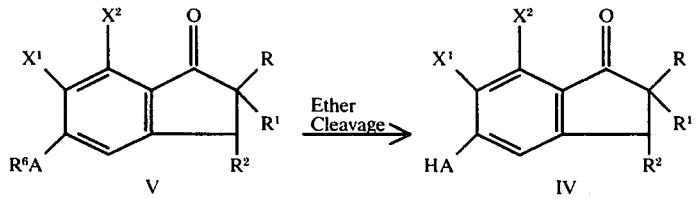

wherein A, R, $R^1$, $R^2$, $X^1$, $X^2$ and $R^6$ are as defined above.

The 2,2-disubstituted-5-lower alkoxy-(or lower alkyl thio)-1-indanones (V, supra) which exhibit uricosuric activity are prepared by treating a 2-substituted-5-lower alkoxy (or lower alkyl thio)-1-indanone (Va, infra) with a suitable alkylating reagent of the formula: $R^1Z$ wherein $R^1$ and Z are as defined above. This reaction is conducted by first treating the 2-substituted-5-lower alkoxy-1-indanone (Va) with a suitable base, for example, an alkali metal hydride such as sodium hydride and the like, or an alkali metal alkoxide, for example, potassium tertiary butoxide and the like. Other bases which may be employed include sodium amide, lithium amide and the like. This basified compound is then treated with the alkylating reagent, $R^1Z$. Any solvent which is inert or substantially inert to the reactants employed may be used. Suitable solvents include, for example, 1,2-dimethoxyethane, tertiary butanol, benzene, dimethylformamide and the like. The reaction may be conducted at a temperature in the range of from about 25° C. to about 150° C. In general, the reaction is conducted at a temperature in the range of from about 75° C. to about 90° C.

The following equation illustrates this process:

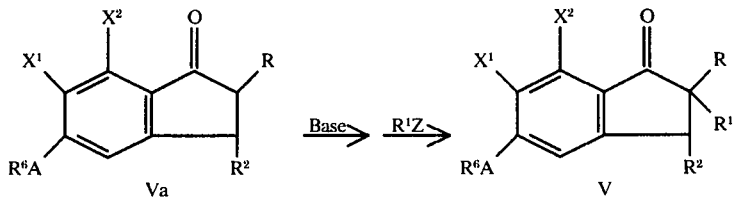

wherein A, R, $R^1$, $R^2$, $R^6$, $X^1$, $X^2$, and Z are as defined above.

An alternative method can also be employed to prepare compounds (of formula V) wherein R is phenyl, substituted phenyl, thienyl or substituted thienyl wherein the substituent is lower alkyl or halo. The starting material in this instance is the 2-$R^1$ compound (Vb) which is reacted first with the strong base, then with a reagent, such as diphenyliodonium halide, or dithienyliodonium halide e.g., the chloride or bromide, as in the following equation:

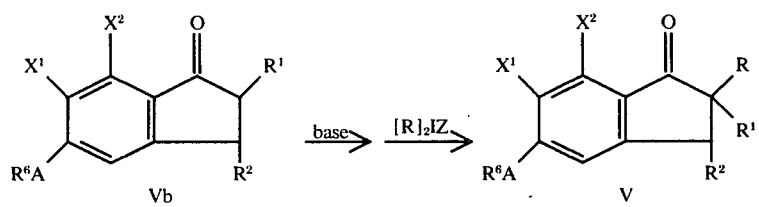

wherein A, $R^1$, $R^2$, $R^6$, $X^1$, $X^2$ and Z are as defined above.

The reaction conditions are as described in the route Va → V, supra.

The 2-substituted-5-lower alkoxy (and lower alkyl thio)-1-indanones (Va, supra) employed above may be prepared by several routes. One route comprising treating the 2-substituted-5-hydroxy-1-indanone with an alkylating agent such as dimethylsulfate or diethylsulfate in the presence of a base such as sodium hydroxide or potassium hydroxide. Other alkylating agents which may be employed include methyl iodide, ethyl iodide and the like employing dimethylformamide as the preferred solvent and as the base, potassium carbonate. The 2-substituted-5-hydroxy-(and 5-mercapto)-1-indanones employed in this particular procedure are known compounds described in U.S. Pat. Nos. 3,668,241 and U.S. 3,704,314.

A second method for preparing the 2-substituted-5-lower alkoxy-(and lower alkyl thio)-1-indanone (Va) comprises the cyclialkylation of a nuclear lower alkoxy (or lower alkyl thio) substituted (2-alkylidenealkanoyl)benzene (VI, infra) by treatment with an electron-acceptor acid, for example, a Lewis acid such as concentrated sulfuric acid, polyphosphoric acid, boron trifluoride and the like. The reaction may be conducted at a temperature in the range of from about 0° C. to about 60° C., in general, the reaction is conducted at ambient temperature. The following equation illustrates this process:

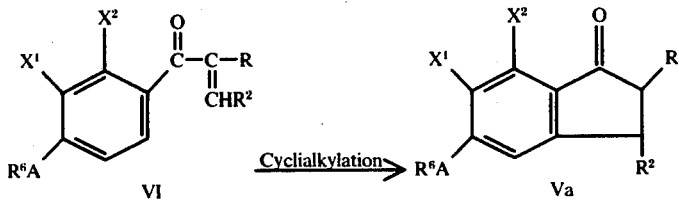

wherein A, R, $R^2$, $R^6$, $X^1$ and $X^2$ are as defined above.

The 2-spiro-5-lower alkoxy-(and lower alkyl thio)-1-indanones (Vb) are prepared by treating a 2-(Ω-haloalkyl)-5-lower alkoxy-(or lower alkylthio)-1-indanone (Vc) with a base, for example, an alkali metal hydride such as sodium hydride and the like in a suitable inert solvent such as 1,2-dimethoxyethane at the reflux temperature of the particular solvent employed. The following equation illustrates this process:

tron-acceptor acid, for example polyphosphoric acid, boron trifluoride, concentrated sulfuric acid and the like. The following equation illustrates this process:

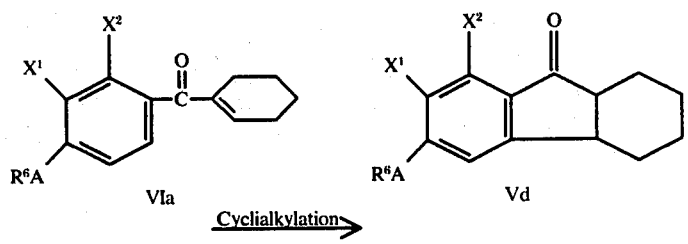

wherein A, R, $R^2$, $R^6$, $X^1$ and $X^2$ are as defined above.

The nuclear lower alkoxy (and lower alkyl thio) (2-alkylidenealkanoyl)benzenes (VI, supra) employed above may be prepared by one of three methods. One method, limited to the preparation of the nuclear lower alkoxy-(or lower alkyl thio)-4-(2-methylenealkanoyl)-

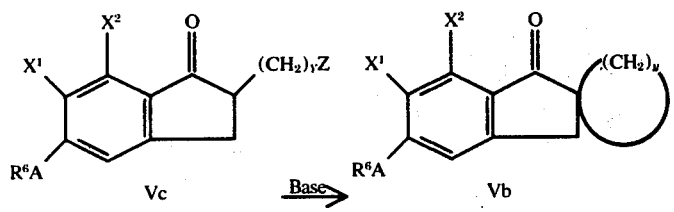

wherein A, $R^6$, $X^1$, $X^2$ and Z are as defined above and Y is an integer having a value of from 3 to 6.

Those compounds wherein R and $R^2$ may be joined to form together with carbon atoms to which they attach a cyclohexyl ring; are prepared by the cyclialkylation of a nuclear lower alkoxy (or lower alkyl thio)substituted cycloalkylidenoyl benzene by treatment with an elecbenzenes (VIb), comprises treating a nuclear lower alkoxy-(or lower alkyl thio)-4-alkanoylbenzene (VII) with dimethylamine hydrochloride and paraformaldehyde followed by treatment of the Mannich intermediate (VIII), thus obtained, with aqueous sodium bicarbonate or anhydrous dimethylformamide, either with or without heat, to afford the desired compound, VIb. The following equation illustrates this process:

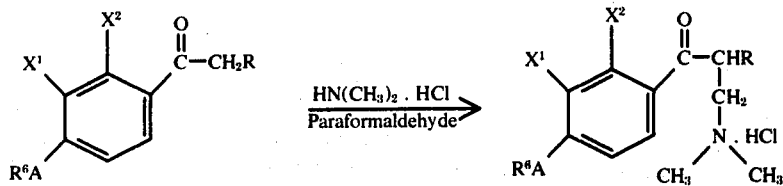

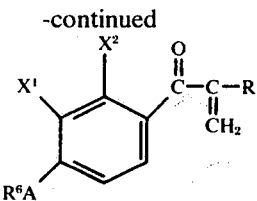

VIb wherein A, R, $R^6$, $X^1$ and $X^2$ are as defined above.

A second method for preparing the nuclear lower alkoxy-(and lower alkyl thio)-2-(alkylidenealkanoyl)-benzenes (VIc), comprises treating a nuclear lower alkoxy-(or lower alkyl thio) substituted 1-bromo-cyclohexanoylbenzene (IX, infra) with a dehydrobrominating agent such as lithium bromide, lithium chloride and the like. Suitable solvents for this reaction include dimethylformamide and the like. This reaction with an appropriate branched chain alkanoyl halide such as 2-methylbutyryl chloride, 2-ethylbutyryl chloride and the like in the presence of a Friedel-Crafts catalyst to afford the corresponding [4-nuclear lower alkoxy (or lower alkyl thio) substituted]alkanoylbenzene (VIIa); which is halogenated and then dehydrohalogenated to afford the 4-(2-alkylidenealkanoyl)-benzene (VId). The following equation illustrates this process:

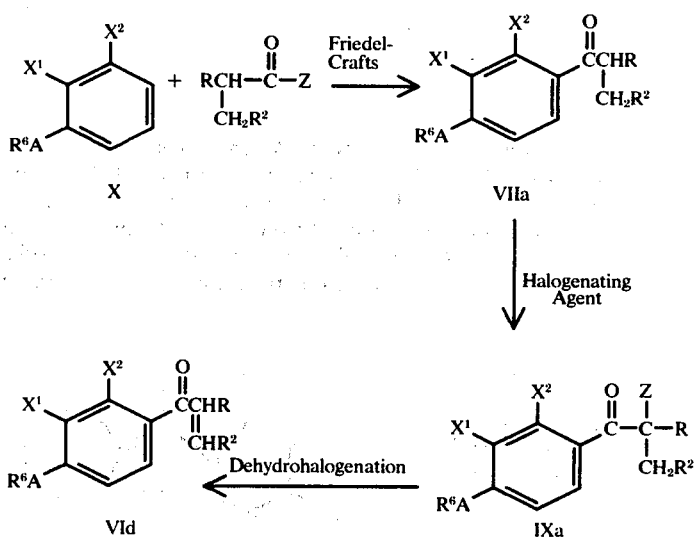

is conveniently conducted at a temperature in the range of from about 50° C. to about 120° C. for a period of time of from about 1 hour to about 6 hours. The following equation illustrates this reaction:

wherein A, R, $R^2$, $R^6$, $X^1$, $X^2$ and Z are as defined above.

A fourth method for preparing compounds of formula VI, and one limited to the preparation of those

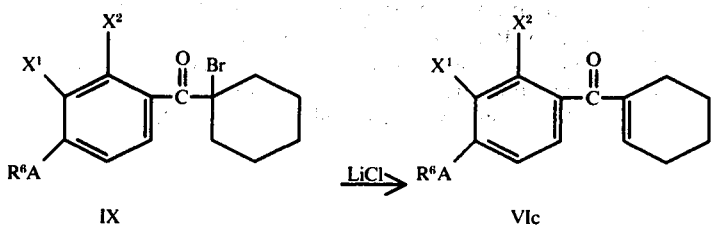

wherein A, $R^6$, $X^1$ and $X^2$ are as defined above.

A third method for preparing the compounds of formula VI and one limited to the preparation of the homologous 4-(2-alkylidenealkanoyl)benzenes VId, for example, the 4-(2-ethylidene) and 4-(2-propylidene) homologs, comprises treating a nuclear lower alkoxy (or lower alkyl thio) substituted benzene (X, infra)

compounds wherein $R^2$ is phenyl, comprises treating a nuclear lower alkoxy (or alkylthio)-4-alkanoylbenzene (VII) with benzaldehyde in a suitable solvent such as water, dimethylsulfoxide and the like in the presence of base such as sodium hydroxide, potassium hydroxide, either with or without heat, to afford the desired compound VIe. The following equation illustrates this process:

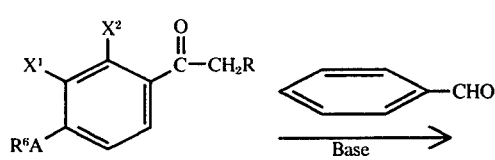

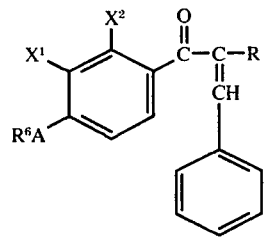

VII          VIe wherein A, R, $R^6$, $X^1$ and $X^2$ are as defined above.

The [4-nuclear lower-alkoxy (and lower alkyl thio)-substituted]alkanoylbenzenes (VII) are either known compounds or may be prepared by the reaction of an alkanoyl halide with a nuclear lower alkoxy (or lower alkyl thio) substituted benzene (X, infra) in the presence of a Friedel-Crafts catalyst such as aluminum wherein A, $R^6$, $X^1$ and $X^2$ are as defined above.

The nuclear lower alkoxy (and lower alkyl thio) substituted cyclohexanoyl benzenes (VIIb) employed above are prepared in a similar manner as described above employing cyclohexanoyl halide in place of the alkanoyl halide described above. The following equation illustrates this reaction:

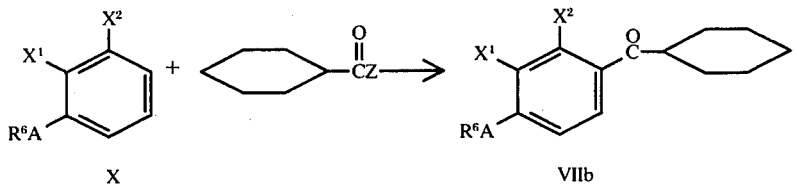

X          VIIb chloride and the like. The reaction solvent and the temperature at which the reaction is conducted are not particularly critical aspects of this reaction inasmuch as any solvent which is inert to the acyl halide and nuclear lower alkoxy (or lower alkyl thio) substituted benzenes may be employed with good results. In this regard, it has been found that methylene chloride is a particularly suitable solvent. The following equation illustrates this reaction:

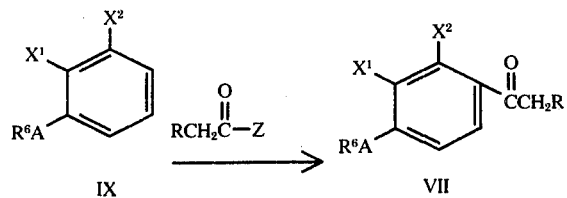

IX          VII wherein A, R, $R^6$, $X^1$, $X^2$ and Z are as defined above.

The nuclear lower alkoxy (and lower alkyl thio) substituted (1-bromo-cyclohexanoyl)benzenes employed above are prepared by the bromination of the correspondingly nuclear lower alkoxy (or lower alkyl thio) substituted (2-cyclohexanoyl)benzene employing standard brominating conditions. The following equation illustrates this process:

wherein A, $R^6$, $X^1$, $X^2$ and Z are as defined above.

As previously mentioned, the non-toxic, pharmacologically acceptable salts of the acids of Compound I & Ia are within the scope of this invention. These salts include those of alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc. These salts are prepared by conventional methods well known in the art. Thus, the acid upon reaction with alkali metal and alkaline earth metal hydroxides, carbonates, bicarbonates, amines or quarternary ammonium hydroxides, forms the corresponding alkali metal, alkaline earth metal, amine or quaternary ammonium salt.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-

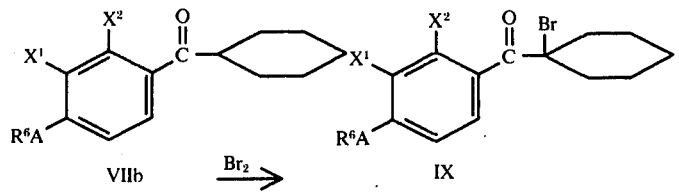

VIIb  $\xrightarrow{Br_2}$  IX methylglucosamine, ephedrine, procaine, tetramethylammonium hydroxide, tetraethylammonium hydroxide, benzyltrimethylammonium and the like.

The salts mentioned above are particularly useful as parenteral solutions because they are very soluble in pharmaceutical carriers such as water or alcohol.

The anhydride derived from the carboxylic acids of Formula I are included in the invention.

Also included within the scope of this invention are the ester and amide derivatives of the instant products which are prepared by conventional methods well known to those skilled in the art. Thus, for example, the ester derivative may be prepared by the reaction of a 1-hydroxy-5-indanyloxy-(or thio)-alkanoic acid of this invention with an alcohol, for example, with a lower alkanol. The amide derivatives may be prepared by converting a 1-hydroxy-5-indanyloxy-(or thio)-alkanoic acid to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding [1-hydroxy-5-indanyloxy-(or thio)-]alkanoic acids.

In addition, to the salts, esters and amides being functionally equivalent to the carboxylic products, those compounds wherein the carboxylic acid is replaced by a 5-tetrazolyl radical are also functionally equivalent to the carboxylic acids. These tetrazole analogs are prepared as depicted in the following equation:

of a base such as potassium carbonate and the like in a suitable solvent such as acetone, dimethylformamide, dimethoxyethane and the like at a temperature in the range of from 25° C. to 100° C. to afford the corresponding nitrile (XI, supra) which, upon treatment with sodium azide and ammonium chloride in dimethylformamide at a temperature in the range of from 25° C. to 100° C., affords the 5-(1-oxo-5-indanyloxymethyl)-tetrazole (XII, supra) which, upon reduction with a metal borohydride or sodium bis(2-methoxyethoxy)aluminum hydride affords the 5(1-hydroxy-5-indanyloxymethyl)tetrazole (XIII, supra).

The instant compounds (I) herein disclosed contain one or more asymmetric carbon atoms (i.e. at positions 1,2 and 3 of the indanyl ring). When this situation exists diasteriomers may be separated by methods well known to those skilled in the art and the optical antipodes may be separated by methods described below. This invention embraces, therefore, not only the racemic [1-hydroxy-5-indanyloxy(or thio)]alkanoic acids but also their optically active antipodes.

Separation of the optical isomers of the racemic acids (I) may be accomplished by forming a salt of the racemic mixture with an optically active base such as (+) or (−) amphetamine, (−)-cinchonidine, dehydroabietylamine, (+) or (−)-α-methylbenzylamine, (+) or (−)-α-(1-naphthyl)-ethylamine, brucine or strychnine and the like in a suitable solvent such as methanol, ethanol, 2-propanol, benzene, acetonitrile, nitromethane, acetone and the like. There is thus formed in the solution two diastereomeric salts one of which is usually more soluble in the solvent than the other. Repetitive recrystallization of the crystalline salt generally affords a pure diasteriomer. The optically pure [1-hydroxy-5-indanyloxy(or thio)]alkanoic acid is obtained by acidification of the salt with a mineral acid, extraction into ether, evaporation of the solvent and recrystallization of the optically pure antipode.

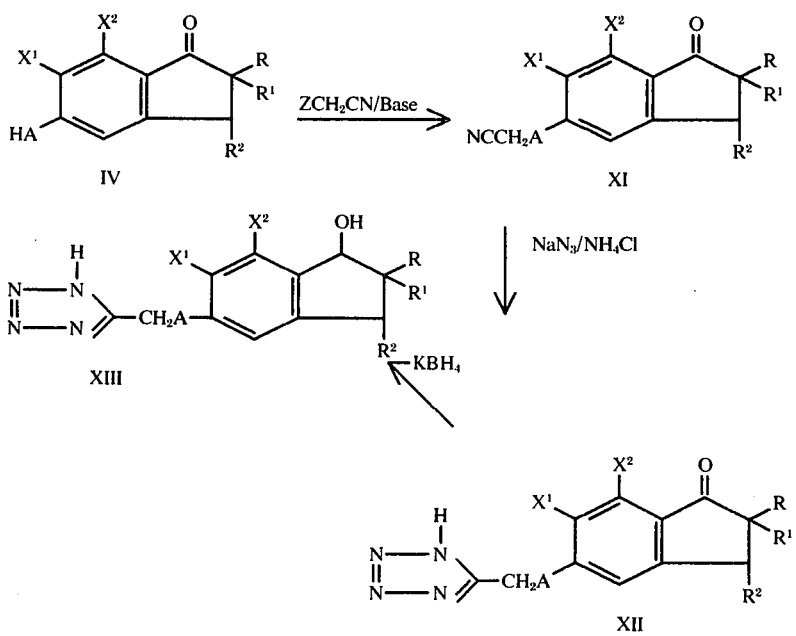

wherein A, R, R¹, R², X¹, X² and Z are as defined above.

The 5-hydroxy-1-indanone (IV) is treated with a haloacetonitrile sch as chloroacetonitrile, bromoacetonitrile or iodoacetonitrile in the presence The other optically pure antipode may generally be obtained by using a different base to form the diastereomeric salt. It is of advantage to isolate the partially resolved acid from the filtrates of the purification of the one diastereomeric salt and to further purify this substance through the use of another optically active base.

Alternatively, the intermediate 5-indanols (II) may be separated into their pure diastereomers and resolved to their pure antipodes before conversion to the instant products (I).

The examples which follow illustrate the [1-hydroxy-5-indanyloxy(or thio)]alkanoic acid products (I) of the invention and the methods by which they are prepared. However, the examples are illustrative only and it will be apparent to those having ordinary skill in the art that all of the products embraced by formula I, supra, may also be prepared in an analogous manner by substituting the appropriate starting materials for those set forth in the examples.

EXAMPLE 1

Preparation of (1-Hydroxy-2-ethyl-6,7-dichloro-5-indanyloxy)-acetic acid

A stirred suspension of (1-oxo-2-ethyl-6,7-dichloro-5-indanyloxy)acetic acid (12.12 g., 0.04 mole) in water (400 ml.) is cooled to 5° C. and treated during a one hour period with solution of potassium borohydride (4.0 g., 0.075 mole) in water (200 ml.). The reaction is stirred for 1 hour then acidified with hydrochloric acid affording 10.6 g. (87%) of (1-hydroxy-2-ethyl-6,7-dichloro-5-indanyloxy)acetic acid which melts at 121°–122° C. after recrystallization from benzene.

Calc.: $C_{13}H_{14}Cl_2O_4$: C, 51.17; H, 4.62; Cl, 23.24. Found: C, 51.30; H, 4.39; Cl, 23.05.

EXAMPLE 2

Preparation of (1-Hydroxy-2-n-propyl-6,7-dichloro-5-indanyloxy)acetic acid

A solution of potassium borohydride (1.2 g., 0.022 mole), water (30 ml.) is added dropwise over a period of 1 hour to a stirred suspension of (1-oxo-2-n-propyl-6,7-dichloro-5-indanyloxy)acetic acid (3.15 g., 0.01 mole). The reaction is stirred at room temperature for 4 hours. The clear solution is cooled in an ice bath and acidified dropwise with concentrated hydrochloric acid to give a white solid which is collected, washed with water, air dried overnight and recrystallized twice from benzene to give 2.3 g. of (1-hydroxy-2-n-propyl-6,7-dichloro-5-indanyloxy)acetic acid, m.p. after drying 110°–112° C.

Calc.: $C_{14}H_{16}Cl_2O_4$: C, 52.68; H, 5.05; Found: C, 52.55; H, 5.09.

EXAMPLE 3

(1-Hydroxy-2-cyclopentyl-6,7-dichloro-5-indanyloxy)acetic acid

Step A: 2',3'-Dichloro-4'-methoxy-2-cyclopentylacetophenone 2,3-Dichloroanisole (57.8 g., 0.327 mole) is dissolved in dichloromethane (300 ml.) and cyclopentylacetyl chloride (52.7 g., 0.367 mole) is added. The solution is cooled to +5° C. and aluminum chloride (48.0 g., 0.36 mole) is added gradually over a one-hour period at +5° C. The mixture is stirred for 2 hours at +5° C. and at 20°–25° C. for 16 hours and then poured into 1 liter of ice water containing 150 ml. of 12N hydrochloric acid. The organic phase is separated and the aqueous phase is extracted with dichloromethane. The combined organic phases are washed with sodium chloride solution, 10% sodium hydroxide and again with sodium chloride solution and dried over magnesium sulfate. On evaporation of the solvent a brown solid is obtained which is crystallized from hexane to obtain 53.2 of 2',3'-dichloro-4'-methoxy-2-cyclopentylacetophenone, m.p. 60°–61.5° C.

Elemental analysis for $C_{14}H_{16}Cl_2O_2$:
Calc.: C, 58.55; H, 5.62;
Found: C, 58.72; H, 5.71.

Step B: 2',3'-Dichloro-4'-methoxy-2-cyclopentylacrylophenone

2',3'-Dichloro-4'-methoxy-2-cyclopentylacetophenone (51.6 g., 0.18 mole) is dissolved in dioxane (460 ml.) and paraformaldehyde (21.6 g., 0.72 mole) and concentrated sulfuric acid (9.65 g.) are added. The mixture is heated at 80°–85° C. for 20 hours. The dioxane is evaporated at reduced pressure. Water is added to the residual gum which then is extracted into ether. The ether extract is washed with water and dried over magnesium sulfate. The ether is evaporated and upon triturating the residue with hexane (5 ml.) there is obtained a solid that is crystallized from ligroin to obtain 2',3'-dichloro-4'-methoxy-2-cyclopentylacrylophenone (33.3 g.), m.p. 59°–63° C. Crystallization from butyl chloride affords a sample (m.p. 66°–67.5° C.) for analysis.

Elemental analysis for $C_{15}H_{16}Cl_2O_2$:
Calc.: C, 60.21; H, 5.37; Found: C, 60.19; H, 5.42.

Step C: 2-Cyclopentyl-5-methoxy-6,7-dichloro-1-indanone

2',3'-Dichloro-4'-methoxy-2-cyclopentylacrylophenone (33.3 g.) is dissolved in 98° sulfuric acid (150 ml.) and stirred at 20° C. for 1.5 hours. The solution then is added dropwise with stirring to ice water. The aqueous phase is decanted from the gummy product and fresh water is added. After 20 hours the gum solidifies and is crystallized from hexane-benzene (3:1) to obtain 2-cyclopentyl-5-methoxy-6,7-dichloro-1-indanone, m.p. 116°–117° C.

Elemental analysis for $C_{15}H_{16}Cl_2O_2$:
Calc.: C, 60.21; H, 5.37; Found: C, 60.29; H, 5.35.

Step D: 2-Cyclopentyl-5-hydroxy-6,7-dichloro-1-indanone

A stirred mixture of 2-cyclopentyl-5-methoxy-6,7-dichloro-1-indanone (14.96 g., 0.05 mole) and pyridine hydrochloride (140 g.) is heated at 175° C. for 2 hours, then poured into water (1500 ml.). The 2-cyclopentyl-5-hydroxy-6,7-dichloro-1-indanone which separates (12.2 g., 86%) melts at 222°–225° C. after recrystallization from ethanol:water, 3:1.

Elemental analysis for $C_{14}H_{14}Cl_2O$: Calc.: C, 58.96; H, 4.95; Found: C, 58,89; H, 5.04.

Step E: 2-Cyclopentyl-6,7-dichloroindan-1,5-diol

To a stirred solution of 2-cyclopentyl-5-hydroxy-6,7-dichloro-1-indanone (8.55 g., 0.03 mole) in tetrahydrofuran (100 ml.) under nitrogen is added dropwise 70% sodium bis-(2-methoxyethoxy)-aluminum hydride in benzene (10 ml.) in tetrahydrofuran (30 ml.) over a ten minute period at 10°–15° C. The reaction mixture is stirred at 25° C. for 3 hours, cooled to 10° C., very slowly treated with 10% hydrochloric acid until frothing ceases, then with 20% hydrochloric acid until acidic. The tetrahydrofuran is decanted from a pasty residue, evaporated to dryness and the residue triturated with benzene to give 7.2 g. of 2-cyclopentyl-6,7-dichloroindan-1,5-diol which melts at 158°–160° C. after crystallization from benzene.

Step F: (1-Hydroxy-2-cyclopentyl-6,7-dichloro-5-indanyloxy)acetic acid

A stirred mixture of 2-cyclopentyl-6,7-dichloroindan-1,5-diol, 2.87 g. (0.01 mole), potassium carbonate, 4.14 g. (0.03 mole), and ethyl bromoacetate, 1.70 g. (0.01 mole) in 30 ml. of dry dimethylformamide is heated at 55°–60° C. for 2 hours under nitrogen, treated with 45 ml. of water and 5 ml. of 10N sodium hydroxide, then heated at 95° C. for 30 minutes and poured into 200 ml. of ice water with vigorous stirring; and then while still ice cold, 1N HCl is added dropwise with stirring until acidic and (1-hydroxy-2-cyclopentyl-6,7-dichloro-5-indanyloxy)acetic acid precipitates.

EXAMPLE 4

Preparation of
[1'-Hydroxy-6',7'-dichlorospiro-(cyclopentane-1,2'-indan)-5'-yloxy]acetic acid Step A: 2,3-Dichloro-4-(6-bromohexanoyl)anisole A stirred mixture of 2,3-dichloroanisole (89 g., 0.50 mole) and 6-bromohexanoyl chloride (120 g., 0.59 mole) is methylene chloride (500 ml.) is cooled to 5° C. and treated with aluminum chloride (74 g., 0.56 mole) in portions during a one-half hour period. The reaction mixture is kept at 25° C. for 18 hours, then poured into ice water (1 liter) containing hydrochloric acid (100 ml.). The organic phase is separated, washed with water, 2% sodium hydroxide, and dilute hydrochloric acid. The methylene chloride is evaporated at reduced pressure, the residual oil dissolved in ether, dried over magnesium sulfate, evaporated to 200 ml. and treated with hexane (600 ml.) affording 2,3-dichloro-4-(6-bromohexanoyl)-anisole which melts at 52°–53° C.

Calcd. for $C_{13}H_{15}BrCl_2O_2$:
C, 44.10; H, 4.27 Found: C, 44.33; H, 4.66

Step B: 2-(4-Chlorobutyl)-5-methyoxy-6,7-dichloro-1-indanone

A stirred mixture of 2,3-dichloro-4-(6-bromohexanoyl)anisole (10 g.), dimethylamine hydrochloride (4 g.), paraformaldehyde (2 g.) and acetic acid (0.5 ml.) is heated on a steam bath for 2 hours, treated with DMF (30 ml.)' and heated an additional 2.5 hours. The reaction mixture is poured into water, extracted with ether, washed with water and dried over magnesium sulfate. Evaporation of the ether affords 9 g. of crude 2,3-dichloro-4-(6-chloro-2-methylenehexanoyl)anisole which is cyclialkylated by treatment with concentrated sulfuric acid (50 ml.). The sulfuric acid solution is poured into water (300 ml.) affording 5.8 g. of 2-(4-chlorobutyl)-5-methoxy-6,7-dichloro-1-indanone which melts at 92° C. after recrystallization from cyclohexane.

Elemental analysis for $C_{14}H_{15}Cl_3O_2$:
Calc.: C, 52.28; H, 4.70; Cl, 33.07; Found: C, 52.25; H, 4.50; Cl, 33.03.

Step C:
5'-Methoxy-6',7'-dichlorospiro-(cyclopentane-1,2'-indanone)

A stirred suspension of sodium hydride (370 mg., 0.0155 mole) in 1,2-dimethoxyethane (250 ml.) is refluxed in an inert atmosphere. A solution of 2-(4-chlorobutyl)-5-methoxy-6,7-dichloro-1-indanone (4.5 g., 0.014 mole) in 1,2-dimethoxyethane (50 ml.) is added over a 20-minute period and refluxing is maintained for 3 hours. The solvent is distilled to a volume a 50 ml. and poured into water (300 ml.) affording 2.6 g. of 5'-methoxy-6',7;-dichlorospiro-(cyclopentane-1,2'-indanone) which melts at 170° C. after recrystallization from ethanol-water.

Elemental analysis for $C_{14}H_{14}Cl_2O_2$:
Calc.: C, 58.97; H, 4.85; Found: C, 59.34; H, 5.08.

Step D: 5'-Hydroxy-6'-,7'-dichlorospiro-(cyclopentane-1,2'-indanone)

A stirred mixture of 5'methoxy-6',7'-dichlorospiro-(cyclopentane-1,2'-indanone) (2.6 g., 0.0091 mole) and pyridine hydrochloride (26 g.) is heated at 185° C. for 1 hour, then poured into water (200 ml.). The 5'-hydroxy-6',7'-dichlorospiro-(cyclopentane-1,2'-indanone) which separates (2.3 g.) melts at 236° C. after recrystallization from nitromethane.

Elemental analysis for $C_{13}H_{12}Cl_2O_2$:
Calc.: C, 57.55; H, 4.46; Found: C, 57.77; H, 4.54.

Step E: 6',7'-Dichlorospiro-(cyclopentane-1,2'-indan)-1',5'-diol

A stirred solution of 5'-hydroxy-6',7'-dichlorospiro-(cyclopentane-1,2'-indanone) (8.1 g., 0.03 mole) in tetrahydrofuran (100 ml.) is cooled to 15° C. and treated over 5 minutes with a solution of sodium bis-(2-methoxy-ethoxy)aluminum hydride (10 ml. of 70% benzene solution). The reaction is stirred one half hour at 25° C., cooled to 10° C., and slowly treated with 20% aqueous hydrochloric acid until acidic. The organic phase is evaporated to an oil, dissolved in ether, washed with water, dried over magnesium sulfate, and the solvent evaporated affording 6.5 g. of 6',7'-dichlorospiro-(cyclopentane-1,2'-indan)-1',5'-diol.

Calc. for $C_{13}H_{14}Cl_2O_2$: C, 57.16; H, 5.17 Found: C, 57.46; H, 5.20

Step F: [1'-Hydroxy-6',7'-dichlorospiro(cyclopentane-1,2'-indan)-5'-yloxy]acetic acid A stirred mixture of 6',7'-dichlorospiro-(cyclopentane-1,2'-indan)-1',5'-diol (4.1 g., 0.015 mole), potassium carbonate (3.6 g.), and ethyl bromoacetate (3.1 ml.) in dimethylformamide (35 ml.) is heated at 55° C. for ½ hour in an inert atmosphere, treated with water (45 ml.), and 10N sodium hydroxide (5 ml.) then heated at 95° C. for ⅓ hour and poured into ice water (200 ml.) containing hydrochloric acid (10 ml.). The [1'-hydroxy-6',7'-dichlorospiro-(cyclopentane-1,2'-indan)-5'-yloxy]-acetic acid which separates melts at 135° C. after recrystallization from benzene.

Calcd. for $C_{15}H_{16}Cl_2O_4$: C, 54.40; H, 4.87; Cl, 21.41. Found: C, 54.03; H, 5.19; Cl, 21.47.

EXAMPLE 5

Preparation of
(1-Hydroxy-2-cyclopentyl-2-methyl-6,7-dichloro-5-indanyloxy)acetic acid ($\alpha$ and $\beta$ isomers)

Step A: 2-Cyclopentyl-2-methyl-5-methoxy-6,7-dichloro-1-indanone

2-Cyclopentyl-5-methoxy-6,7-dichloro-1-indanone (7.5 g., 0.025 mole) Example 3, Step C, is dissolved in dry 1,2-dimethoxyethane (200 ml.) under nitrogen. Sodium hydride (57% in mineral oil; 1.16 g., 0.027 mole) is then added and the mixture is stirred at 80° C. until evolution of hydrogen ceases (2 hours). The solution is cooled and methyl iodide (7.5 ml.) is added, the mixture is again brought to reflux and then cooled. Most of the 1,2-dimethoxyethane is evaporated and water is added to the residue which soon solidifies and is crystallized from methylcyclohexane and from ethanol-water (4:1) to obtain 3.4 g. of 2-cyclopentyl-2- methyl-5-methoxy-6,7-dichloro-1-indanone, m.p. 109°–111.5° C.

Elemental analysis for $C_{17}H_{18}Cl_2O_2$:
Calc.: C, 61.35; H, 5.79; Found: C, 61.71; H, 5.84.

Step B: 2-Cyclopentyl-2-methyl-5-hydroxy-6,7-dichloro-1-indanone

2-Cyclopentyl-2-methyl-5-methoxy-6,7-dichloro-1-indanone (3.4 g., 0.0109 mole) is added to dry heptane (180 ml.) and aluminum chloride (4.36 g., 0.0327 mole) is added. The mixture is refluxed for 1 hour and the hexane is decanted from the gummy residue which then is added to ice water (200 ml.) containing 12N hydrochloric acid (15 ml.). The solid that separates is crystallized from benzene to obtain 2.77 g. of 2-cyclopentyl-2-methyl-5-hydroxy-6,7-dichloro-1-indanone, m.p. 190°–194° C.

Elemental analysis for $C_{16}H_{16}Cl_2O_2$: Calc.: C, 60.21; H, 5.37; Found: C, 60.43; H, 5.41.

Step C: 2-Cyclopentyl-2-methyl-6,7-dichloroindan-1,5-diol ($\alpha$ and $\beta$ isomers)

To a stirred solution of 2-cyclopentyl-2-methyl-5-hydroxy-6,7-dichloro-1-indanone (8.4 g., 0.028 mole) in tetrahydrofuran (100 ml.) under nitrogen is added dropwise over a 10 minute period [70% sodium bis-(2-methoxyethoxy)-aluminum hydride is benzene] (10 ml.) in tetrahydrofuran (30 ml.) maintaining the reaction temperature at 10°–15° C. The reaction mixture is stirred at 25° C. for 23 hours, cooled to 10° C., very slowly treated with 10% hydrochloric acid until frothing ceased, then with 20% hydrochloric acid until acidic. The tetrahydrofuran is decanted from a pasty residue, evaporated to dryness, the residue taken up in benzene, dried over magnesium sulfate the evaporated to give 6.2 g. of 2-cyclopentyl-2-methyl-6,7-dichloroindan-1,5-diol (isomer mixture). Four recrystallizations from benzene gives 1.9 g. of 2-cyclopentyl-2-methyl-6,7-dichloroindan-1,5-diol ($\alpha$ isomer), m.p. 187°–189° C.

Calc. for $C_{15}H_{18}Cl_2O_2$: C, 59.81; H, 6.02 pmr (dmso-d6) Found: C, 60.00; H, 6.30 $\delta$= 0.70 (S,3, $CH_3$)

From the mother liquors of the recrystallization of 2-cyclopentyl-2-methyl-6,7-dichloroindan-1,5-diol ($\alpha$ isomer) is obtained 2-cyclopentyl-2-methyl-6,7-dichloroindan-1,5-diol ($\beta$ isomer) pmr (dmso-d6):$\delta$= 1.00 (S,3,$CH_3$).

Step D: (1-Hydroxy-2-cyclopentyl-2-methyl-6,7-dichloro-5-indanyloxy)acetic acid ($\alpha$ isomer)

A stirred mixture of 2-cyclopentyl-2-methyl-6,7-dichloroindan-1,5-diol ($\alpha$ isomer) (1.9 g., 0.0063 mole), potassium carbonate (1.3 g., 0.0095 mole) and ethylbromoacetate (1.5 g. 0.0095 mole) in dimethylformamide (20 ml.) is warmed at 55°–60° C. under nitrogen for 2 hours, then treated with water (20 ml.) and 10N sodium hydroxide (1.9 ml.) and heated on a steam bath for one-half hour. The reaction mixture is poured into ice water (300 ml.) and while ice cold, 1N HCl is added dropwise with stirring to give 1.36 g. of (1-hydroxy-2-cyclopentyl-2-methyl-6,7-dichloro-5-indanyloxy)acetic acid ($\alpha$ isomer) which melts at 129°–131° C. after crystallization from benzene : hexane, 1:1.

Elemental analysis for $C_{17}H_{20}Cl_2O_4$: Calc.: C, 56.83; H, 5.61; Found: C, 57.14; H, 5.69.

Step E: (1-Hydroxy-2-cyclopentyl-2-methyl-6,7-dichloro-5-indanyloxy)acetic acid ($\beta$ isomer)

By following substantially the procedure described in Example 5, Step D, but substituting for the 2-cyclopentyl-2-methyl-6,7-dichloroindan-1,5-diol ($\alpha$ isomer) an equivalent amount of 2-cyclopentyl-2-methyl-6,7-dichloroindan-1,5-diol ($\beta$ isomer) there is obtained (1-hydroxy-2-cyclopentyl-2-methyl-6,7-dichloro-5-indanyloxy)acetic acid ($\beta$ isomer).

EXAMPLE 6

(1-Hydroxy-2,2-dimethyl-6,7-dichloro-5-indanyloxy)acetic acid

Step A: 2',3'-Dichloro-4'-methoxyisobutyrophenone

A stirred mixture of 2,3-dichloroanisole (100 g., 0.565 mole) and isobutyryl chloride (66 g., 0.62 mole) in methylene chloride (400 ml.) is cooled to 5° C. and treated with aluminum chloride (83 g., 0.62 mole) during a 1-hour period. The reaction mixture is allowed to warm to 25° C. and after 24 hours is poured into ice water (400 ml.) and hydrochloric acid (30 ml.). The organic phase is washed with 5% sodium hydroxide, water, dried over magnesium sulfate and distilled at reduced pressure affording 68 g. of 2',3'-dichloro-4'-methoxyisobutyrophenone which distills at 120°–130° C./0.5 mm.

Elemental analysis for $C_{11}H_{12}Cl_2O_2$: Calc.: C, 53.46; H, 4.89; Found: C, 54.25; H, 5.07.

Step B: 2Bromo-2',3'-dichloro-4'-methoxyisobutyrophenone

A stirred solution of 2',3'-dichloro-4'methoxyisobutyrophenone (45 g., 0.183 mole) in acetic acid (150 ml.) is treated during ½ hour with bromine (30 g., 0.187 mole). The reaction mixture is stirred 10 minutes, then poured into ice water (600 ml.) containing sodium bisulfite (2 g.). The 2-bromo-2'-3'-dichloro-4'-methoxyisobutyrophenone which separates (48 g.) melts at 72°–73° C. after recrystallization from hexane.

Elemental analysis for $C_{11}H_{11}BrCl_2O_2$: Calc.: C, 40.52; H, 3.40; Found: C, 40.68; H, 3.38.

Step C: 2-Methylene-2',3'-dichloro-4'-methoxypropiophenone

A solution of 2-bromo-2',3'-dichloro-4'-methoxyisobutyrophenone (32 g., 0.1 mole) and anhydrous lithium bromide (17.4 g., 0.2 mole) in DMF (200 ml.) is stirred at 95° C. in an inert atmosphere for 3 hours and poured into ice water (500 ml.). The 2-methylene-2',3'-dichloro-4'-methoxypropiophenone which separates melts at 59° C. after recrystallization from petroleum ether.

Elemental analysis for $C_{11}H_{10}Cl_2O_2$: Calc.: C, 53.90, H, 4.11; Found: C, 53.72; H, 4.11.

Step D: 2-Methyl-5-methoxy-6,7-dichloro-1-indanone

A solution of 2-methylene-2',3'-dichloro-4'-methoxypropiophenone (40 g., 0.163 mole) in concentrated sulfuric acid (75 ml.) is allowed to stand at 25° C. for 24 hours and then is slowly poured into vigorously stirred ice water (500 ml.). The 2-methyl-5-methoxy-6,7-dichloro-1-indanone which separates (40 g.) melts at 129° C. after recrystallization from methylcyclohexane.

Elemental analysis for $C_{11}H_{10}Cl_2O_2$: Calc.: C, 53.90; H, 4.11; Found: C, 53.84; H, 4.00.

Step E: 2,2-Dimethyl-5-methoxy-6,7-dichloro-1-indanone

A stirred suspension of 2-methyl-5-methoxy-6,7-dichloro-1-indanone (12.2 g., 0.05 mole) and sodium hydride (1.43 g., 0.06 mole) in anhydrous 1,2-dimethoxyethane (500 ml.) is heated in an inert atmosphere at 80°–85° C. for 1 hour, cooled to 30° C. and treated with methyl iodide (8 ml.). The reaction mixture is refluxed for 15 minutes, then the solvent is distilled at reduced pressure. The crude product is poured into water (500 ml.), extracted into ether, washed with water and dried over magnesium sulfate. After evaporation of the ether the product is crystallized from methylcyclohexane affording 8.2 g. of 2,2-dimethyl-5-methoxy-6,7-dichloro-1-indanone which melts at 142° C.

Elemental analysis for $C_{12}H_{12}Cl_2O_2$: Calc.: C, 55.62; H, 4.67; Found: C, 55,80; H, 4.69.

Step F: 2,2-Dimethyl-5-hydroxy-6,7-dichloro-1-indanone

A stirred suspension of 2,2-dimethyl-5-methoxy-6,7-dichloro-1-indanone (12.2 g., 0.047 mole) and aluminum chloride (15.5 g., 0.116 mole) in heptane (500 ml.) is refluxed for 1 hour and cooled. The heptane is decanted from the reaction mixture and the solid residue is poured into ice (500 g.) and concentrated hydrochloric acid (50ml.). The product which separates (7.6 g.) melts at 273° C. after crystallization from nitromethane.

Elemental analysis for $C_{11}H_{10}Cl_2O_2$: Calc.: C, 53.90; H, 4.11; Found: C, 53.30; H, 4.12.

Step G: 2,2-Dimethyl-6,7-dichloro-1,5-indanediol 2,2-Dimethyl-6,7-dichloro-1,5-indanediol is prepared following substantially the same procedure described in Example 4, Step E, using the following substances: 2,2-dimethyl-5-hydroxy-6,7-dichloro-1-indanone (6.1 g., 0.025 mole); sodium bis-(2-methoxyethoxy)-aluminum hydride (70% in benzene) 8 ml.; tetrahydrofuran (75 ml.). The above procedure gives 2,2-dimethyl-6,7-dichloro-1,5-indanediol.

Step H: (1-Hydroxy-2,2-dimethyl-6,7-dichloro-5-indanyloxy)acetic Acid (1-Hydroxy-2,2-dimethyl-6,7-dichloro-5-indanyloxy)acetic acid is prepared following substantially the same procedure described in Example 4, Step F, using the following substances: 2,2-dimethyl-6,7-dichloro-1,5-indanediol (3.7 g., 0.015 mole); potassium carbonate (3.6 g.); ethyl bromoacetate (3.1 ml.); and dimethylformamide (35 ml.), and hydrolyzing the resultant ester with aqueous sodium hydroxide in accordance with Example 4, Step F, gives (1-hydroxy-2,2-dimethyl-6,7-dichloro-5-indanyloxy)acetic acid.

EXAMPLE 7

(1-Hydroxy-2-isopropyl-2-methyl-6,7-dichloro-5-indanyloxy)-acetic Acid

Step A: 2',3'-Dichloro-4'-methoxyisolvalerophenone

A stirred mixture of 2,3-dichloroanisole (265 g., 1.50 mole) and isovaleryl chloride (200 g., 1.64 mole) in methylene chloride (1.2 l.) is cooled to 5° C. and treated with aluminum chloride (220 g., 1.64 mole) during a 2-hour period. The reaction is allowed to warm to 25° C. and after 24 hours is poured into ice water (3 l.) and hydrochloric acid (600 ml.). The organic phase is washed with 10% sodium hydroxide and water and dried over magnesium sulfate. After evaporation of the solvent, the product is crystallized from hexane affording 295 g. of 2',3'-dichloro-4'-methoxyisovalerophenone which melts at 49°-54° C.

Elemental analysis for $C_{12}H_{14}Cl_2O_2$: Calc.: C, 55.19; H, 5.40; Found: C, 55.38; H, 5.51.

Step B: 2-Methylene-2',3'-dichloro-4'-methoxyisovalerophenone

A stirred mixture of 2',3'-dichloro-4'-methoxyisovalerophenone (261.6 g., 1.0 mole), paraformaldehyde (75.0 g., 2.5 mole), dimethylamine hydrochloride (327 g., 4.0 mole) and acetic acid (26 ml.) is heated on a steam bath for 18 hours, treated with DMF (500 ml.), heated an additional three hours, then poured into ice water (1.7 l.). The crude product which separates is dissolved in benzene (600 ml.) and dried over sodium sulfate. Evaporation of the benzene affords 237 g. of 2-methylene-2',3'-dichloro-4'-methoxyisovalerophenone which melts at 46°–51° C. and is used in Step C without further purification.

Step C: 2-Isopropyl-5-methoxy-6,7-dichloro-1-indanone

A solution of the product of Step B (237 g.) in concentrated sulfuric acid (400 ml.) is stirred at 25° C. for 2 hours, then slowly added to a copious amount of ice water. The product which separates is triturated with fresh water, neutralized with aqueous sodium bicarbonate, filtered and dried. Recrystallization from benzene-hexane affords 134 g. of 2-isopropyl-5-methoxy-6,7-dichloro-1-indanone which melts at 118°–119° C.

Elemental analysis for $C_{13}H_{14}Cl_2O_2$: Calc.: C, 57.16; H, 5.17. Found: C, 57.23; H, 5.33.

Step D: 2-Methyl-2-isopropyl-5-methoxy-6,7-dichloro-1-indanone

A stirred suspension of 2-isopropyl-5-methoxy-6,7-dichloro-1-indanone (7.3 g., 0.025 mole) and sodium hydride (810 mg., 0.028 mole) in anhydrous 1,2-dimethoxyethane(250 ml.) is heated in an inert atmosphere at 80°–85° C. for 1 hour, cooled to 30° C. and treated with methyl iodide (6 ml.). The reaction mixture is heated to 80° C., then the solvent is distilled at reduced pressure and the residue poured into ice water. The 2-methyl-2-isopropyl-5-methoxy-6,7-dichloro-1-indanone which separates (7.0 g.) melts at 143° C. after recrystallization from ethanol-water.

Elemental analysis for $C_{14}H_{16}Cl_2O_2$: Calc.: C, 58.55; H, 5.62; Found: C, 58.82; H, 5.60.

Step E: 2-Methyl-2-isopropyl-5-hydroxy-6,7-dichloro-1-indanone

A stirred suspension of 2-methyl-2-isopropyl-5-methoxy-6,7-dichloro-1-indanone (7.0 g., 0.0244 mole) and aluminum chloride (9.0 g., 0.068 mole) in heptane (400 ml.) is refluxed for 1 hour and cooled. The heptane is decanted from the reaction mixture and the solid residue is poured into water (300 ml.) and concentrated hydrochloric acid (20 ml.). The crude product is extracted into ether (300 ml.), washed with water, dried over magnesium sulfate, distilled to a volume of 100 ml. and treated with hexane (100 ml.). The 2-methyl-2-isopropyl-5-hydroxy-6,7-dichloro-1-indanone which separates (6.5 g.) melts at 215° C.

Elemental analysis for $C_{13}H_{14}Cl_2O_2$: Calc.: C, 57.16; H, 5.17; Found: C, 56.90; H, 5.15.

Step F: 2-Methyl-2-isopropyl-6,7-dichloro-1,5-indandiol

2-Methyl-2-isopropyl-6,7-dichloro-1,5-indan-diol is prepared following substantially the same procedure described in Example 4, Step E, using the following substances: 2-methyl-2-isopropyl-5-hydroxy-6,7-dichloro-1-indanone (8.2 g., .03 mole); sodium bis-(2-methoxyethoxy)aluminum hydride (70% in benzene [10 ml.]; and tetrahydrofuran (100 ml.).

The above procedure gives 2-methyl-2-isopropyl-6,7-dichloro-1,5-indandiol.

Step G: (1-Hydroxy-2-isopropyl-2-methyl-6,7-dichloro-5-indanyloxy)acetic Acid (1-Hydroxy-2-isopropyl-2-methyl-6,7-dichloro-5-indanyloxy)acetic acid is prepared following substantially the same procedure described in Example 4, Step F, using the following substances: 2-methyl-2-isopropyl-6,7-dichloro-1,5-indandiol (8.3 g., .03 mole); potassium carbonate (7.2 g.); ethyl bromoacetate (6.2 ml.); and dimethylformamide (70 ml.); and hydrolyzing the resultant ester with aqueous sodium hydroxide in accordance with Example 4, Step F, gives (1-hydroxy-2-isopropyl-2-methyl-6,7-dichloro-5-indanyloxy)acetic acid.

EXAMPLE 8

(1-Hydroxy-2-benzyl-2-methyl-6,7-dichloro-5-indanyloxy)-acetic Acid

Step A: 2-Benzyl-2-methyl-5-methoxy-6,7-dichloro-1-indanone

Potassium tert-butoxide (1.68 g., 0.015 mole) in dry tert-butyl alcohol (40 ml.) is added to a refluxing solution of 2methyl-5-methoxy-6,7-dichloro-1indanone in benzene (50 ml.). After refluxing for 30 minutes, benzyl bromide (1.72 g., 0.01 mole) in benzene (10 ml.) is added dropwise. After refluxing for an additional 30 minutes the mixture is cooled, water (10 ml.) is added and the mixture is evaporated to dryness. The residue is washed with water and taken up with ether. The ether solution is washed with water and a saturated sodium chloride solution, dried over sodium sulfate and evaporated. The syrupy residue of 2-benzyl-2-methyl-5-methoxy-6,7-dichloro-1-indanone (3 g.) is used directly in the next step without purification.

Step B: 2-Benzyl-2-methyl-5-hydroxy-6,7-dichloro-1-indanone

2-Benzyl-2-methyl-5methoxy-6,7-dichloro-1-indanone (6 g.) is mixed with pyridine hydrochloride (60 g.) and the mixture is heated at 180° C. for 3 hours. The dark liquid is poured into water (1 l.) and the dark powdery product is collected and crystallized from acetic acid to obtain 2-benzyl-2-methyl-5-hydroxy-6,7-dichloro-1-indanone (2 g.), m.p. 219° -221° C. The product is identified by its nuclear magnetic resonance spectrum.

NMR: (DMSO-D$_6$) -δ11.5 (1S- -OH); δ7.2 (5S - aromatic); δ6.9 (1S - aromatic); δ1.1 (3S- -CH$_3$);

Step C: 2-Benzyl-2-methyl-6,7-dichloro-1,5-indandiol

2-Benzyl-2-methyl-6,7-dichloro-1,5-indandiol is prepared following substantially the same procedure described in Example 4, Step E, using the following substances: 2-benzyl-2-methyl-5-hydroxy-6,7-dichloro-1-indanone (4.8 g., 0.015 mole); sodium bis-(2-methoxyethoxy)-aluminum hydride (70% in benzene [5 ml.]); and tetrahydrofuran (50 ml.).

The above procedure gives 2-benzyl-2-methyl-6,7-dichloro-1,5-indandiol.

Step D: (1-Hydroxy-2-benzyl-2-methyl-6,7-dichloro-5-indanyloxy)acetic Acid (1-Hydroxy-2-benzyl-2methyl-6,7-dichloro-5-indanyloxy)acetic acid is prepared following subtantially the same procedure described in Example 4, Step F, using the following substances: 2-benzyl-2-methyl-6,7-dichloro-1,5indandiol (4.8 g., 0.015 mole); potassium carbonate (3.6 g.); ethyl bromoacetate (3.1 ml.); and dimethylformamide (35 ml.), and hydrolyzing the resultant ester with aqueous sodium hydroxide in accordance with Example 4, Step F, gives (1-hydroxy-2-benzyl-2-methyl-6,7-dichloro-5-indanyloxy)acetic acid.

EXAMPLE 9

5-(1-Hydroxy-2-ethyl-6,7-dichloro-5-indanyloxymethyl)tetrazole

Step A: (1-Oxo-2-ethyl-6,7-dichloro-5-indanyloxy)-acetonitrile

A mixture of 2-ethyl-5-hydroxy-6,7-dichloroindanone (24.5 g., 0.1 mole), anhydrous potassium carbonate (13.8 g., 0.10 mole), chloroacetonitrile (7.55 g., 0.10 mole) and potassium iodide (1.66 g.) in acetone (0.5 l.) is refluxed for 18 hours. The product which precipitates upon addition of water to the reaction mixture (20 g., 71%) melts at 139°–141° C. after recrystallization from butyl chloride.

Elemental analysis for C$_{13}$H$_{11}$Cl$_2$NO$_2$;
Calc.: C, 54.95; H, 3.90; N, 4.93;
Found: C, 55.09; H, 3.89; N, 4.92.

Step B: 5-(1-Oxo-2-ethyl-6,7-dichloro-5-indanyloxymethyl)tetrazole

A mixture of (1-oxo-2-ethyl-6,7-dichloro-5-indanyloxy)acetonitrile (7.5 g., 0.0265 mole), sodium azide (2.02 g., 0.031 mole) and ammonium chloride (1.68 g., 0.0031 mole) in dimethylformamide (40 ml.) is heated on a steam bath for one hours and poured into dilute aqueous hydrochloric acid affording 7.3 g. (85%) of 5-(1-oxo-2-ethyl-6,7-dichloro-5-indanyloxymethyl)tetrazole which melts at 205°–206° C. after recrystallization from nitromethane.

Elemental analysis for C$_{13}$H$_{12}$Cl$_2$N$_4$O$_2$:
Calc.: C, 47.72; H, 3.70; N, 17.13;
Found: C, 47.47; H, 3.37; N, 17.30.

Step C: 5-(1-Hydroxy-2-ethyl-6,7-dichloro-5-indanyloxymethyl)tetrazole 5-(1-Hydroxy-2-ethyl-6,7-dichloro-5-indanyloxymethyl)tetrazole is prepared following substantially the same procedure described in Example 1, using the following substances: 5-(1-oxo-2-ethyl-6,7-dichloro-5-indanyloxymethyl)tetrazole (6.54 g., 0.02 mole); potassium borohydride (2.0 g.); and water (200 ml.).

The above procedure gives 5-(1-hydroxy-2-ethyl-6,7-dichloro-5-indanyloxymethyl)tetrazole.

EXAMPLE 10

(1-Hydroxy-2-cyclopentyl-2,6-dimethyl-7-chloro-5-indanyloxy)-acetic Acid

Step A: 2'-Chloro-3'-methyl-4'-methoxy-2-cyclopentylacetophenone

By following substantially the procedure described in Example 3, Step A, using the following substances: 2-methyl-3-chloroanisole (36.5 g., 0.234 mole), cyclopentylacetyl chloride (37.7 g., 0.257 mole), aluminum chloride (34.3 g., 0.257 mole) and methylene chloride (250 ml.) there is obtained 50 g. (80%) of 2'-chloro-3'-methyl-4'-methoxy-2-cyclopentylacetophenone which distills at 140°–165° C./0.6 mm.

Elemental analysis for C$_{15}$H$_{19}$ClO$_2$:
Calc. C, 67.54; H, 7.18;
Found: C, 67.53; H, 7.41.

Step B: 2'-Chloro-3'-methyl-4'-methoxy-2-cyclopentylacrylophenone

By following substantially the procedure described in Example 3, Step B, using the following substances: 2'-chloro-3'-methyl-4'-methoxy-2-cyclopentylacetophenone (45 g., 0.169 mole), paraformaldehyde (12.6 g., 0.42 mole), dimethylamine hydrochloride (61 g., 0.75 mole) and acetic acid (4.2 ml.) there is obtained 36.3 g. (78%) of 2'-chloro-3'-methyl-4'- methoxy-2-cyclopentylacrylophenone which after recrystallization from petroleum ether melts at 45°–46.5° C.

Elemental analysis for $C_{16}H_{16}ClO_2$:
Calc. C, 68.93; H, 6.87;
Found: C, 69.02; H, 6.96.

Step C: 2-Cyclopentyl-5-methoxy-6-methyl-7-chloro-1-indanone

By following substantially the procedure described in Example 3, Step C, using the following substances: 2'-chloro-3'-methyl-4'-methoxy-2-cyclopentylacrylophenone (36.3 g.) and sulfuric acid (200 ml.) there is obtained 30.7 g. (85%) of 2-cyclopentyl-5-methoxy-6-methyl-7-chloro-1-indanone which after recrystallization from hexane melts at 73°–74° C.

Elemental analysis for $C_{16}H_{19}ClO_2$:
Calc.: C, 68.93; H, 6.87;
Found: C, 69.08; H, 6.76.

Step D: 2-Cyclopentyl-2,6-dimethyl-5-methoxy-7-chloro-1-indanone

By following substantially the procedure described in Example 5, Step A, using the following substances: 2-cyclopentyl-5-methoxy-6-methyl-7-chloro-1-indanone (2.79 g., 0.01 mole), sodium hydride (0.264 g., 0.011 mole), 1,2-dimethoxyethane (100 ml.) and methyl iodide (3.11 ml., 0.05 mole) there is obtained 2.8 g. (96%) of 2-cyclopentyl-2,6-dimethyl-5-methoxy-7-chloro-1-indanone which melts at 48°–52° C. after purification by chromatography.

Elemental analysis for $C_{17}H_{21}ClO_2$:
Calc.: C, 69.73; H, 7.23;
Found: C, 69.68; H, 7.33.

Step E: 2-Cyclopentyl-2,6-dimethyl-5-hydroxy-7-chloro-1-indanone

By following substantially the procedure described in Example 3, Step B, using the following substances: 2-cyclopentyl-2,6-dimethyl-5-methoxy-7-chloro-1-indanone (5.4 g., .0184 mole), aluminum chloride (7.36 g., 0.552 mole) and heptane (200 ml.), there is obtained 3.3 g. of 2-cyclopentyl-2,6-dimethyl-5-hydroxy-7-chloro-1-indanone, m.p. 175°–177° C. from ethanol-water.

Elemental analysis for $C_{16}H_{19}ClO_2$:
Calc.: C, 68.93; H, 6.87;
Found: C, 69.07; H, 6.71.

Step F: 2-Cyclopentyl-2,6-dimethyl-7-chloroindan-1,5-diol

2-Cyclopentyl-2,6-dimethyl-7-chloroindan-1,5-diol is prepared following substantially the same procedure described in Example 4, Step E, using the following substances: 2-cyclopentyl-2,6-dimethyl-5-hydroxy-7-chloro-1-indanone (8.37 g., 0.03 mole); sodium bis-(2-methoxyethoxy)-aluminum hydride (70% in [10 ml.]); and tetrahydrofuran (100 ml.).

The above procedure gives 2-cyclopentyl-2,6-dimethyl-7-chloroindan-1,5-diol.

Step G: (1-Hydroxy-2-cyclopentyl-2,6-dimethyl-7-chloro-5-indanyloxy)acetic Acid (1-Hydroxy-2-cyclopentyl-2,6-dimethyl-7-chloro-5-indanyloxy)acetic acid is prepared following substantially the same procedure described in Example 4, Step F, using the following substances: 2-cyclopentyl-2,6-dimethyl-7-chloroindan-1,5-diol (4.2 g., 0.015 mole); potassium carbonate (3.6 g.); ethyl bromoacetate (3.1 ml.); and dimethylformamide (35 ml.), and hydrolyzing the resultant ester with aqueous sodium hydroxide in accordance with Example 4, Step F, there is obtained (1-hydroxy-2-cyclopentyl-2,6-dimethyl-7-chloro-5-indanyloxy)acetic acid.

EXAMPLE 11

α,α-Dimethyl-(1-hydroxy-2-cyclopentyl-2-methyl-6,7-dichloro-5-indanyloxy)acetic Acid To a refluxing solution of 2-cyclopentyl-2-methyl-6,7-dichloro-1,5-indandiol (Example 5, Step C), (15.6 g., 0.05 mole) in acetone (500 ml.) in an inert atmosphere is added solid sodium hydroxide (12.6 g., 0.25 mole). Chloroform (7.6 g., 0.69 mole) in acetone (50 ml.) is added dropwise during a ten-minute period. The reaction mixture is refluxed for 5 hours, then evaporated to dryness at reduced pressure. The residue is dissolved in water, filtered and acidified with hydrochloric acid affording α,α-dimethyl-(1-oxo-2-cyclopentyl-2-methyl-6,7-dichloro-5-indanyloxy)acetic acid.

EXAMPLE 12

4-(1-Hydroxy-2-cyclopentyl-2-methyl-6,7-dichloro-5-indanyloxy)butyric Acid

By following the procedure described in Example 4, Step F, using as the reagents 2-cyclopentyl-2-methyl-6,7-dichloroindan-1,5-diol (Example 5, Step C), (31 g., 0.1 mole), potassium carbonate (15.2 g., 0.11 mole), DMF (200 ml.), ethyl 4-bromobutyrate (23.5 g., 0.11 mole), water (200 ml.) and 10 N sodium hydroxide (40 ml.), there is obtained 4-(1-hydroxy-2-cyclopentyl-2-methyl-6,7-dichloro-5-indanyloxy)butyric acid.

EXAMPLE 13

3-(1-Hydroxy-2-cyclopentyl-2-methyl-6,7-dichloro-5-indanyloxy)propionic Acid.

2-Cyclopentyl-2-methyl-6,7-dichloroindan-1,5-diol (Example 5, Step C) (15.6 g., 0.05 mole) is dissolved in a 10% sodium hydroxide solution (50 ml.). The solution is heated to reflux and beta-propiolactone, (36.0 g., 0.5 mole) is added at such as to keep the reaction mixture refluxing. The reaction mixture is kept basic by the addition of 10% sodium hydroxide. The reaction mixture is cooled and acidified with dilute hydrochloric acid. The product is extracted with ether and extracted from the other solution with a 5% solution of sodium bicarbonate. Acidification affords the desired product.

EXAMPLE 14

(1-Hydroxy-2-cyclopentyl-2-methyl-6,7-dichloro-5-indanylthio)acetic Acid

Step A: 2',3'-Dichloro-4'-methylthio-2-cyclopentylacetophenone

2',3'-Dichloro-4'-methylthio-2-cyclopentylacetophenone is prepared following substantially the same procedure described in Example 3, Step A, using the following substances: 2,3-dichlorothioanisole (63.1 g., 0.327 mole), methylene chloride (300 ml.), cyclopentylacetyl chloride (52.7 g., 0.367 mole) and aluminum chloride (48.0 g., 0.36 mole).

Step B: 2',3'-Dichloro-4'-methylthio-2-cyclopentylacrylophenone

2',3'-dichloro-4'-methylthio-2-cyclopentylacrylophenone is prepared following substantially the same procedure described in Example 3, Step B, using the following substances: 2',3'-dichloro-4'-methylthio-2-cyclopentylacetophenone (54.5 g., 0.18 mole), paraformaldehyde (21.6 g., 0.72 mole), concentrated sulfuric acid (9.65 g.) and dioxane (450 ml.).

Step C: 2-Cyclopentyl-5-methylthio-6,7-dichloro-1-indanone

2-Cyclopentyl-5-methylthio-6,7-dichloro-1-indanone is prepared following substantially the same procedure described in Example 3, Step C, using the following substances: 2',3'-dichloro-4'-methylthio-2-cyclopentylacrylophenone (10 g.) and concentrated sulfuric acid (50 ml.).

Step D: 2-Cyclopentyl-2-methyl-5-methylthio-6,7-dichloro-1-indanone

2-Cyclopentyl-2-methyl-5-methylthio-6,7-dichloro-1-indanone is prepared following substantially the same procedure described in Example 5, Step A, using the following substances: 2-cyclopentyl-5-methylthio-6,7-dichloro-1-indanone (7.9 g., 0.025 mole), 1,2-dimethoxyethane (200 ml.), sodium hydride (660 mg., 0.0275 mole) and methyl iodide (7.5 ml.).

Step E: 2-Cyclopentyl-2-methyl-5-mercapto-6,7-dichloro-1-indanone

To a stirred suspension of 2-cyclopentyl-2-methyl-5-methylthio-6,7-dichloro-1-indanone (3.59 g., 0.01 mole) in liquid ammonia (100 ml.) cooled in a dry-ice-acetone bath is added sodium (460 mg., 0.02 gr. atom) in small portions until a permanent blue color persists. Ammonium chloride (1.0 g.) is added, the excess ammonia is evaporated and the reaction mixture is dissolved in water, acidified and extracted with ether which is washed with water, dried over magnesium sulfate and evaporated at reduced pressure affording 2-cyclopentyl-2-methyl-5-mercapto-6,7-dichloro-1-indanone.

Step F: 2-Cyclopentyl-2-methyl-5-mercapto-6,7-dichloro-1-indanone

By following substantially the procedure described in Example 4, Step E, using the following substances: 2-cyclopentyl-2-methyl-5-mercapto-6,7-dichloro-1-indanone (8.97 g., .03 mole); sodium bis-(2-methoxyethoxy)-aluminum hydride (70% in benzene [10 ml.]); and tetrahydrofuran (100 ml.); there is obtained 2-cyclopentyl-2-methyl-5-mercapto-6,7-dichloro-1-indanone.

EXAMPLE 14

Step G: (1-Hydroxy-2-cyclopentyl-2-methyl-6,7-dichloro-5-indanylthio)acetic acid (1-Hydroxy-2-cyclopentyl-2-methyl-6,7-dichloro-5-indanylthio)acetic acid is prepared following substantially the same procedure described in Example 4, Step F, using the following substances: 2-cyclopentyl-2-methyl-5-mercapto-6,7-dichloro-1-indanol (4.5 g., 0.015 mole); potassium carbonate (3.6 g.); ethyl bromoacetate (3.1 ml.); and dimethylformamide (35 ml.); and hydrolyzing the resultant ester with aqueous sodium hydroxide in accordance with Example 4, Step F, there is obtained (1-hydroxy-2-cyclopentyl-2-methyl-6,7-dichloro-5-indanylthio)acetic acid.

EXAMPLE 15

1,2-Dichloro-5α,5,6,7,8,8α-hexahydro-9-hydroxyfluoren-3-yloxy)acetic Acid

Step A: Cyclohexyl 2,3-dichloro-4-methoxyphenyl ketone

A stirred mixture of 2,3-dichloroanisole (88.5 g., 0.5 mole) and cyclohexanecarbonyl chloride (81 g., 0.55 mole) in methylene chloride (400 ml.) is cooled to 5° C. and treated with aluminum chloride (74 g., 0.55 mole) during a ½ hour period. The reaction is allowed to warm to 25° C. and after 16 hours is poured into ice water (1 l.) and hydrochloric acid (200 ml.). The organic phase is washed with 10% sodium hydroxide and saturated salt solution, and dried over magnesium sulfate. After evaporation of the solvent, the product is crystallized from hexane to give 42.3 g. of cyclohexyl 2,3-dichloro-4-methoxyphenyl ketone which melts at 97°–98° C.

Elemental analysis for $C_{14}H_{16}Cl_2O_2$:
Calc.: C, 58.55; H, 55.62;
Found: C, 58.92; H, 5.64.

Step B: 1-Bromocyclohexyl 2,3-dichloro-4-methoxyphenyl ketone

Bromine (22.4 g., 0.14 mole) in acetic acid (50 ml.) is added dropwise to a stirred solution of cyclohexyl-2,3-dichloro-4-methoxyphenyl ketone (40 g., 0.14 mole) and 30% hydrobromic acid (0.5 ml.) in acetic acid (400 ml.) during a 1½ hour period at 25° C. The mixture is poured into water (1.5 l.) and sodium bisulfite (10 g.). The product which precipitates is crystallized from cyclohexane to give 47.3 g. of 1-bromocyclohexyl 2,3-dichloro-4-methoxyphenyl ketone which melts at 94°–95° C.

Elemental analysis for $C_{14}H_{15}BrCl_2O_2$:
Calc.: C, 45.93; H, 4.13;
Found: C, 45.79; H, 4.11.

Step C: 1-Cyclohexenyl 2,3-dichloro-4-methoxyphenyl ketone

1-Bromocyclohexyl 2,3-dichloro-4-methoxyphenyl ketone (47.3 g., 0.13 mole), lithium chloride (16.5 g., 0.39 mole) and dimethylformamide (200 ml.) are heated at 90° C for 2 hours, then poured into water (1 l.) to give 36.5 g. of 1-cyclohexenyl 2,3-dichloro-4-methoxyphenyl ketone which melts at 126°–129° C. after drying at 60° C. under vacuum for 16 hours.

Elemental analysis for $C_{14}H_{14}Cl_2O_2$:
Calc.: C, 58.96; H, 4.95;
Found: C, 58.87; H, 5.10.

Step D: 1α,1,2,3,4,4α-Hexahydro-6-methoxy-7,8-dichlorofluoren-9-one

A stirred mixture of 1-cyclohexenyl 2,3-di-chloro-4-methoxyphenyl ketone (34 g., 0.12 mole) and polyphosphoric acid (340 g.) is heated at 90° C. for 17 hours in a resin pot. Crushed ice (1 kg.) is added to precipitate the product which on crystallization from benzene:cyclohexane, 1:1, gives 18.4 g. of 1α,1,2,3,4,-,4α-hexahydro-6-methoxy-7,8-dichlorofluoren-9-one which melts at 169°–171° C.

Elemental analysis for $C_{14}H_{14}Cl_2O_2$:
Calc.: C, 58.96; H, 4.95;
Found: C, 59.35; H, 5.43.

Step E: 1α,1,2,3,4,4α-Hexahydro-6-hydroxy-7,8-dichlorofluoren-9-one

A stirred mixture of 1α,1,2,3,4,4α-hexahydro-6-methoxy-7,8-dichlorofluoren-9-one (4.0 g. 0.014 mole) and pyridine hydrochloride (40 g.) is heated at 170° C. for 2 hours, then poured into water (800 ml.). The 1α,1,2,3,4,4α-hexahydro-6-hydroxy-7,8-dichlorofluoren-9-one which separates (3.75 g.) melts at 212°–219° C. after recrystallization from ethanol.

Elemental analysis for $C_{13}H_{12}Cl_2O_2$:
Calc.: C, 57.58; H, 4.46;
Found: C, 57.12; H, 4.53.

Step F: (1,2-Dichloro-5α,5,6,7,8,8α-hexahydro-9-oxofluoren-3-yloxy)acetic Acid

A stirred mixture of 1α,1,2,3,4,4α-hexahydro-6-hydroxy-7,8-dichlorofluoren-9-one (3.55 g., 0.0131 mole), potassium carbonate (3.62 g., 0.0262 mole) and ethyl bromoacetate (4.37 g., 0.0262 mole) in dimethylformamdie (30 ml.) is warmed at 55°–60° C. under nitrogen for three hours, then treated with potassium hydroxide (1.90 g., 0.0288 mole) in methanol (30 ml.) and heated on a stream bath for three hours. The reaction mixture is poured into water (500 ml.) and acidified with 12N hydrochloric acid to precipitate 2.00 g. of (1,2-dichloro-5α,5,6,7,8,8αacidified 9-oxo-fluoren-3-yloxy)acetic acid which melts at 202°–206° C. after recrystallization from acetic acid: water, 3:2.

Elemental analysis for $C_{15}H_{14}Cl_2O_4$:
Calc.: C, 54.73; H, 4.29;
Found: C, 54.84; H, 4.37.

Step G: (1,2-Dichloro-5α,5,6,7,8,8α-hexahydro-9-hydroxy-fluoren-3-yloxy)acetic acid A stirred suspension of (1,2-dichloro-5α,5,6,7, 8,8α-hexahydro-9-oxo-fluoren-3-yloxy)acetic acid (0.01 mole) in water (100 ml.) is cooled to 5° C. and treated over a 1 hour period with a solution of potassium borohydride (0.02 mole) in water (100 ml.). The reaction is stirred for 4 hours. The reaction is acidified dropwise with hydrochloric acid, separating (1,2-dichloro-5α,5,6,7, 8,8α-hexahydro-9-hydroxy-fluoren-3-yloxy)acetic acid which is recrystallized from benzene.

EXAMPLE 16

(1-Hydroxy-2-ethyl-3-phenyl-6,7-dichloro-5-indanyloxy)-acetic Acid

Step A: 2',3'-Dichloro-4'-methoxybutyrophenone

A solution of 2',3'-dichloro-4'-hydroxy-butryophenone (57 g., 0.0248 mole) in methanol (400 ml.) is heated to reflux. A solution of sodium hydroxide (40 g.) in water (100 ml.) and dimethyl sulfate are added alternatively in small portions over a ½ hour period such that the reaction mixture is always alkaline. On cooling, 2',3'-dichloro-4'-methoxybutyrophenone separates which melts at 42°–44° C. after recrystallization from hexane.

Elemental analysis for $C_{11}H_{12}Cl_{12}O_2$:
Calc.: C, 53.46; H, 4.89;
Found: C, 53.71; H, 4.93.

Step B: 2,3-Dichloro-4-(2-benzylidenebutyryl)anisole

A stirred mixture of benzaldehyde (19.4 g., 0.183 mole) and 2',3'-dichloro-4'-methoxybutyrophenone (42.2 g., 0.183 mole) in ethanol (350 ml.) is treated with 20% sodium hydroxide (35.9 ml.). The reaction is stirred for 22 hours during which time the 2,3-dichloro-4-(2-benzylidenebutyryl)anisole separates, m.p. 127°–130° C.

Elemental analysis for $C_{18}H_{16}Cl_2O_2$:
Calc.: C, 64.49; H, 4.81;
Found: C, 64.39; H, 4.79.

Step C: 2-Ethyl-3-phenyl-5-methoxy-6,7-dichloro-1-indanone

A stirred mixture of 2,3-dichloro-4-(2-benzylidenebutyryl)anisole (55.6 g., 0.166 mole) and polyphosphoric acid (550 g.) is heated at 95°–100° C. for 6 hours than at 80°–85° C. for 16 hours, and then poured into water (2 l.) affording 2-ethyl-3-phenyl-5-methoxy-6,7-dichloro-1-indanone which melts at 114°–116° C. after recrystallization from acetic acid-water.

Elemental analysis for $C_{18}H_{16}Cl_2O_2$:
Calc.: C, 64.49; H, 4.48;
Found: C, 64.48; H, 4.87.

Step D: 2-Ethyl-3-phenyl-5-hydroxy-6,7-dichloro-1-indanone

A stirred mixture of 2-ethyl-3-phenyl-5-methoxy-6,7-dichloro-1-indanone (13.9 g., 0.0415 mole) and aluminum chloride (13.6 g., 0.104 mole) in heptane (120 ml. is refluxed for five hours then cooled. The heptane is decanted, and the residue is treated with ice water (100 ml.) containing hydrochloric acid. The gum which separates is extracted into ether, washed with water, dried over magnesium sulfate, and the ether evaporated at reduced pressure affording 11.3 g. of 2-ethyl-3-phenyl-5-hydroxy-6,7-dichloro-1-indanone which melts at 220°–222° C. after recrystallization from methanol.

Elemental analysis for $C_{17}H_{14}Cl_2O_2$:
Calc.: C, 63.57; H, 4.39.
Found: C, 63.80; H, 4.46.

Step E: (1-Oxo-2-ethyl-3-phenyl-6,7-dichloro-5-indanyloxy)-acetic Acid (1-Oxo-2-ethyl-3-phenyl-6,7-dichloro-5-indanyloxy)acetic acid is prepared following substantially the same procedure described in Example 4, Step F, using the following substances: 2-ethyl-3-phenyl-5-hydroxy-6,7-dichloro-1-indanone (16.6 g., 0.0518 mole); potassium carbonate (14.4 g., 0.104 mole); ethyl bromoacetate (17.3 g., 0.104 mole); and dimethylformamide (80 ml.); and hydrolyzing the resultant ester in accordance with Example 4, Step F, there is obtained 14.4. g. (74%) of (1-oxo-2-ethyl-3-phenyl-6,7-dichloro-5-indanyloxy)acetic acid which after recrystallization from acetic acid melts at 203°–206° C.

Elemental analysis for $C_{19}H_{16}Cl_2O_4$:
Calc.: C, 60.17; H, 4.25;
Found: C, 60.50; H, 4.40.

Step F: (1-Hydroxy-2-ethyl-3-phenyl-6,7-dichloro-5-indanyloxy)acetic Acid (1-Hydroxy-2-ethyl-3-phenyl-6,7-dichloro-5-indanyloxy)acetic acid is prepared following substantially the same procedure described in Example 1, using the following substances: (1-oxo-2-ethyl-3-phenyl-6,7-dichloro-5-indanyloxy)acetic acid (7.58 g., 0.02 mole); potassium borohydride (2.0 g.); and water (200 ml.). Follwing this procedure, there is obtained (1-hydroxy-2-ethyl-3-phenyl-6,7-dichloro-5-indanyloxy)acetic acid.

EXAMPLE 17

(1-Hydroxy-2-phenyl-2-methyl-6,7-dichloro-5-indanyloxy)acetic Acid

Step A: 2-Phenyl-2-methyl-5-methoxy-6,7-dichloro-1-indanone

Potassium tert-butoxide (8.42 g., 0.075 mole) in dry tert-butyl alcohol (300 ml.) is added to a refluxing solution of 2-methyl-5-methoxy-6,7-dichloro-1-indanone, (12.26 g., 0.05 mole) prepared as described in Example 6, Steps A to D, in benzene (50 ml.). After refluxing for 2 hours a suspension of diphenyliodonium chloride (19.0 g., 0.06 mole) in tert-butyl alcohol (1 liter) is added dropwise. After refluxing for an additional 2 hours the mixture is cooled, water (300 ml.) is added and the mixture is evaporated to dryness in vacuo to give 4.97 g. of 2-phenyl-2-methyl-5-methoxy-6,7-dichloro-1-indanone which melts at 161°–163° C. after crystallization from benzene:cyclohexane, 1:2.

Step B: 2-Phenyl-2-methyl-5-hydroxy-6,7-dichloro-1-indanone

2-Phenyl-2-methyl-5-methoxy-6,7-dichloro-1-indanone (4.94 g., 0.015 mole) is mixed with pyridine hydrochloride (50 g.) and the mixture is heated at 175° C.

for 1 hour, then poured into water (500 ml.) and the product is collected and crystallized from ethanol:water, 2:1 to obtain 2-phenyl-2-methyl-5-hydroxy-6,7-dichloro-1-indanone, m.p. 194°–6° C.

Step C: 2-Methyl-2-phenyl-6,7-dichloroindan-1,5-diol ($\alpha$ and $\beta$ isomers)

To a stirred solution of 2-methyl-2-phenyl-5-hydroxy-6,7-dichloro-1-indanone (14.3 g., 0.047 mole) in tetrahydrofuran (150 ml.) under nitrogen is added dropwise over a 10 minute period 70% sodium bis(2-methoxyethoxy) aluminum hydride in benzene (17 ml.) in tetrahydrofuran (50 ml.) while maintaining the reaction temperature at 10°–15° C. The reaction mixture is stirred at 25° C. for 26 hours, cooled to 10° C, slowly treated with 10% hydrochloric acid until frothing ceases, then with 20% hydrochloric acid until acidic. The tetrahydrofuran is decanted from a pasty residue, evaporated to dryness and the residue taken up in benzene (300 ml.). The insoluble, homogeneous product which separates at this stage is primarily 2-methyl-2-phenyl-6,7-dichloroindane-1,5-diol ($\alpha$-isomer), 800 mg., m.p. 177°–181° C. and is used without further purification. The benzene solution is dried over magnesium sulfate and evaporated to dryness to give 8.57 g. of a mixture of isomers. Three crystallizations from benzene gives 3.0 g. of 2-methyl-2-phenyl-6,7-dichloroindan-1,5-diol ($\beta$-isomer), m.p. 163°–165° C. and is used in Example 18 below without further purification.

Step D: (1-Hydroxy-2-methyl-2-phenyl-6,7-dichloro-5-indanyloxy)acetic acid ($\alpha$-isomer)

A stirred mixture of 2-methyl-2-phenyl-6,7-dichloroidan-1,5-diol ($\alpha$-isomer) (800 mg., 0.0026 mole), potassium carbonate (715 mg., 0.0052 mole) and ethylbromoacetate (866 mg., 0.0052 mole) in dimethylformamide (15 ml.) is warmed at 55°–60° C. for 2.5 hours, then treated with water (15 ml.) and 10N sodium hydroxide solution (10ml., 0.01 mole) and heated at 100° C. for 1 hour. The reaction mixture is poured into a solution of ice-water (50 ml.) and 12N hydrochloric acid (10 ml.) to precipitate 520 mg. of (1-hydroxy-2-methyl-2-phenyl-6,7-dichloro-5-indanyloxy)acetic acid ($\alpha$-isomer) which melts at 178°–179° C. after crystallization from benzene:hexane, 1:1.

Elemental analysis for $C_{18}H_{16}Cl_2O_4$:
Calc.: C, 58.6; H, 4.9;
Found: C, 58.9; H, 4.4.

EXAMPLE 18

(1-Hydroxy-2-methyl-2-phenyl-6,7-dichloro-5-indanyloxy)-acetic acid ($\beta$-isomer)

Step A: (1-Hydroxy-2-methyl-2-phenyl-6,7-dichloro-5-indanyloxy)acetic acid ($\beta$-isomer)

A stirred mixture of 2-methyl-2-phenyl-6,7-dichlorinan-1,5-diol ($\beta$-isomer) (3.00 g., 0.0097 mole), potassium carbonate (2.68 g., 0.0194 mole) in dimethylformamide (60 ml.) is warmed at 55°–60° C. for 2.5 hours, then treated with water (60 ml.) and 10N sodium hydroxide solution (4 ml., 0.04 mole) and heated at 100° C. for 1 hour. The reaction mixture is poured into a solution of ice-water (600 ml.) and 12N hydrochloric acid (20 ml.) to precipitate 920 mg. of (1-hydroxy-2-methyl-2-phenyl-6,7-dichloro-5-indanyloxy)acetic acid ($\beta$-isomer) which melts at 160°–162° C. after crystallization from benzene: hexane, 1:1.

Elemental analysis for $C_{18}H_{16}Cl_2O_4$:

Calc.: C, 58.55; H, 4.91;
Found: C, 58.85; H, 4.50.

As mentioned previously, the novel components of this invention are diuretic and saluretic agents. When administered to patients in therapeutic dosages in conventional vehicles, the instant products effectively reduce the amount of sodium and chloride ions in the body, lower dangerous excesses of fluid levels to acceptable levels and in general, alleviate conditions usually associated with edema or fluid retention.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) in a wide variety of therapeutic dosages in conventional vehicles as, for example by oral administration in the form of a table or by intravenous injection. In addition, the compounds may be formulated into suppositories or as a salve for topical administration or they may be administered sublingually. Also, the daily dosage of the products may be varied over a wide range as, for example, in the form of scored tablets containing 0.25, 1, 5, 10, 25, 50, 100, 150, 200, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 mg. of [1-hydroxy-5-indanyloxy(or thio)]alkanoic acid (I) or a suitable salt, ester or amide derivative thereof, with 149 mg. of lactose and 1 mg. of magnesium sterate and placing the 200 mg. mixture into a No. 1 gelatin capsule. Similary, by employing more of the active ingredient and less lactose, other dosage forms can be put up in No. 1 gelatin capsules and, should it be necessary to mix more than 200 mg. of ingredients together, larger capsules may be employed. Compressed tables, pills, or other desired unit dosages can be prepared to incorporate the compounds of this invention by conventional methods, and if desired, can be made up as elixirs or as injectable solutions by methods well known to pharmacists. An effective amount of the drug is ordinarily supplied at a dosage level of from about 1 mg. to about 20 mg./kg. of body weight. Preferably the range is from about 1 mg. to 10 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following example is inclnded to illustrate the preparation of a representative dosage form:

EXAMPLE 19

Dry-filled capsules containing 50 mg. of active ingredient per capsule.

|  | Per capsule |
|---|---|
| (1-Hydroxy-2-methyl-2-phenyl-6,7-dichloro-5-indanyloxy)acetic acid | 50 mg. |
| Lactose | 149 mg. |
| Magnesium Stearate | 1 mg. |
| Capsule (Size No. 1) | 200 mg. |

The (1-hydroxy-2-methyl-2-phenyl-6,7-dichloro-5-indanyloxy) acetic acid is reduced to a No. 60 powder and then lactose and magnesium sterate are passed through a No. 60 bolting cloth onto the powder and the combined ingredients admixed for 10 minutes and then filled into a No. 1 dry gelatin capsule.

Similr dry-filled capsules can be prepared by replacing the active ingredient of the above example by any of the other novel compounds of this invention.

It will be apparent from the foregoing description that the [1-hydroxy-5-indanyloxy(or thio)]alkanoic acid products (I) of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula:

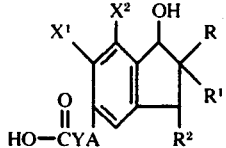

wherein A is oxygen; R is lower alkyl, cycloalkyl having from 3–6 nuclear carbon atoms, phenyl, substituted phenyl wherein the substituent is lower alkyl or halo; $R^1$ is hydrogen, lower alkyl, phenyl lower alkyl, phenyl, substituted phenyl wherein the substituent is lower alkyl or halo, or R and $R^1$ may be joined, together with the carbon atom to which they are attached, to form cycloalkyl; $R^2$ is hydrogen, phenyl, or lower alkyl or $R^1$ and $R^2$, taken together with the carbon atoms to which they are attached, is cycloalkyl; $X^1$ is hydrogen, methyl or halo; and $X^2$ is methyl or halo; or $X^1$ and $X^2$ may be joined to form a hydrocarbylene chain containing 3 or 4 carbon atoms; and Y is alkylene or haloalkylene containing a maximum of 4 carbon atoms, a non-toxic, pharmacologically acceptable salt thereof or a lower alkyl ester derivative thereof.

2. A compound according to claim 1 of the formula:

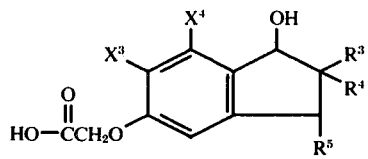

wherein $R^5$ is hydrogen or phenyl; $R^3$ is lower alkyl, cycloalkyl having from 3 - 6 nuclear carbon atoms, phenyl or substituted phenyl wherein the substituents are lower alkyl or halo; $R^4$ is hydrogen or lower alkyl; or $R^3$ and $R^4$ can be joined together with the carbon atoms to which they are attached, to form a cycloalkyl radial containing from 5 to 6 nuclear carbon atoms; $X^3$ and $X^4$ are the same or different radicals selected from methyl or chloro a non-toxic, pharmacologically acceptable salt thereof or a lower alkyl ester derivative thereof.

3. A compound according to claim 2 wherein $R^5$ is hydrogen; $R^3$ is cyclopentyl; $R^4$ is methyl and $X^3$ and $X^4$ are chloro.

4. A compound according to claim 2 wherein $R^5$ is hydrogen; $R^3$ is isopropyl; $R^4$ is methyl and $X^3$ and $X^4$ are chloro.

5. A compound according to claim 2 wherein $R^5$ is hydrogen; $R^3$ and $R^4$ are methyl and $X^3$ and $X^4$ are chloro.

6. A compound according to claim 2 wherein $R^4$ are $R^5$ are hydrogen; $R^3$ is ethyl; and $X^3$ and $X^4$ are chloro.

7. A compound according to claim 2 wherein $R^5$ is phenyl; $R^3$ is ethyl; $R^4$ is methyl and $X^3$ and $X^4$ are chloro.

8. A compound according to claim 2 wherein $R^5$ is hydrogen; $R^3$ and $R^4$ are joined to form cyclopentyl radical and $X^3$ and $X^4$ are chloro.

9. A compound according to claim 2 wherein $R^3$ is hydrogen; $R^4$ and $R^5$ are joined to form a cyclohexyl radical and $X^3$ and $X_4$ are chloro.

10. A compound according to claim 2 wherein $R^3$ is phenyl; $R^4$ is methyl; $R^5$ is hydrogen and $X^3$ and $X^4$ are chloro.

11. A compound according to claim 2 wherein $R^3$ is p-chlorophenyl; $R^4$ is methyl; $R^5$ is hydrogen and $X^3$ and $X^4$ are chloro.

12. A pharmaceutical composition useful in the treatment of edema and hypertension which also maintains uric acid at predetermined levels or causes a decrease which comprises 50 mg. to 500 mg. of a compound of the formula:

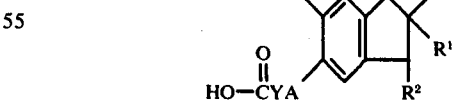

wherein A is oxygen, R is lower alkyl, cycloalkyl having from 3 - 6 nuclear carbon atoms, phenyl and substituted phenyl wherein the substituent is halo or lower alkyl; $R^1$ is hydrogen, lower alkyl, phenyl lower alkyl, phenyl, substituted phenyl wherein the substituent is lower alkyl or halo; or R and $R^1$ may be joined to form a cycloalkyl; $R^2$ is hydrogen, phenyl or lower alkyl or $R^1$ and $R^2$ taken together with the carbon atoms to which they are attacked, is cycloalkyl; $X^1$ is hydrogen, methyl, or halo and $X^2$ is methyl or halo or $X^1$ and $X^2$ may be joined to form a hydrocarbylene chain containing 3 to 4 carbon atoms and Y is alkylene or haloalkylene containing a maximum of 4 carbon atoms, a non-toxic, pharmacologically acceptable salt thereof or a lower alkyl ester derivative thereof and a pharmaceutically acceptable carrier.

13. A method for the treatment of edema and hypertension in a patient which comprises administering thereto a unitary dosage of from 50 to 500 mg. of a compound of the formula:

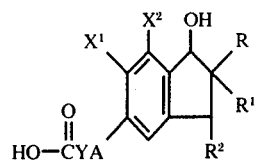

wherein A is oxygen, R is lower alkyl, cycloalkyl having from 3 – 6 nuclear carbon atoms, phenyl and substituted phenyl wherein the substituent is halo or lower alkyl; $R^1$ is hydrogen, lower alkyl, phenyl lower alkyl, phenyl, substituted phenyl wherein the substituent is lower alkyl or halo; or R and $R^1$ may be joined to form a cycloalkyl; $R^2$ is hydrogen, phenyl or lower alkyl or $R^1$ and $R^2$ taken together with the carbon atoms to which they are attached, is cycloalkyl; $X^1$ is hydrogen, methyl, or halo and $X^2$ is methyl or halo or $X^1$ and $X^2$ may be joined to form a hydrocarbylene chain containing 3 to 4 carbon atoms and Y is alkylene or haloalkylene containing a maximum of 4 carbon atoms, a non-toxic, pharmacologically acceptable salt thereof or a lower alkyl ester derivative thereof in a total daily dose of from 50 mg. to 2000 mg.

* * * * *

UNITED STATES PATENT OFFICE
CERTIFICATE OF CORRECTION

PATENT NO. : 4,012,524
DATED : March 15, 1977
INVENTOR(S) : Edward J. Cragoe, Jr. and Otto W. Woltersdorf, Jr.

It is certified that error appears in the above—identified patent and that said Letters Patent are hereby corrected as shown below:

Col. 36, line 15 - "radial" should read --radical--.

Col. 36, line 29 - "are" should read --and--.

Col. 36, line 48 - "predetermined" should read --pretreatment--.

Col. 36, line 68 - "attacked" should read --attached--.

Signed and Sealed this

Thirty-first Day of May 1977

[SEAL]

Attest:

RUTH C. MASON
Attesting Officer

C. MARSHALL DANN
Commissioner of Patents and Trademarks